United States Patent
Matsubara et al.

(10) Patent No.: US 8,896,840 B2
(45) Date of Patent: Nov. 25, 2014

(54) INTERFEROMETRIC METHOD AND DIGITAL HOLOGRAPHIC MICROSCOPE

(75) Inventors: Isao Matsubara, Utsunomiya (JP); Chung-Chieh Yu, Tucson, AZ (US); Yasuyuki Unno, Utsunomiya (JP); William Dallas, Tucson, AZ (US)

(73) Assignee: Canon Kabushiki Kaisha, Tokyo (JP)

( * ) Notice: Subject to any disclaimer, the term of this patent is extended or adjusted under 35 U.S.C. 154(b) by 211 days.

(21) Appl. No.: 13/455,931

(22) Filed: Apr. 25, 2012

(65) Prior Publication Data

US 2013/0286403 A1 Oct. 31, 2013

(51) Int. Cl.
*G01B 9/021* (2006.01)

(52) U.S. Cl.
USPC ......................................... 356/458

(58) Field of Classification Search
USPC ................... 356/457, 458; 359/10, 22–24, 32
See application file for complete search history.

(56) References Cited

U.S. PATENT DOCUMENTS

| | | | | |
|---|---|---|---|---|
| 6,038,067 A | * | 3/2000 | George | 359/368 |
| 7,289,255 B2 | * | 10/2007 | Baba et al. | 359/35 |
| 7,649,160 B2 | | 1/2010 | Colomb et al. | |
| 7,920,271 B2 | * | 4/2011 | Vakoc et al. | 356/479 |
| 8,384,907 B2 | * | 2/2013 | Tearney et al. | 356/456 |
| 2009/0125242 A1 | | 5/2009 | Choi et al. | |

FOREIGN PATENT DOCUMENTS

WO 2008123408 A1 10/2008

OTHER PUBLICATIONS

Wonshik Choi et al., Tomographic Phase Microscopy, Nature Methods, vol. 4, No. 9, pages, Sep. 2007, 717-719, Nature Publishing Group.

Christopher Fang-Yen et al., Video-rate Tomographic Phase Microscopy, Journal of Biomedical Optics 16(1), Jan. 10, 2005 (Jan. 2011), 1-5.

* cited by examiner

*Primary Examiner* — Michael A Lyons
(74) *Attorney, Agent, or Firm* — Canon U.S.A., Inc. IP Division

(57) ABSTRACT

An interferometric method for detecting information about a sample includes emitting a laser beam; splitting the laser beam into a reference beam and an object beam; transmitting the object beam through the sample in an incident angle; combining the reference beam with the object beam passed through the sample to form an interference pattern; detecting the interference pattern, and non-linearly scanning the object beam in order to detect a plurality of interference patterns.

8 Claims, 34 Drawing Sheets

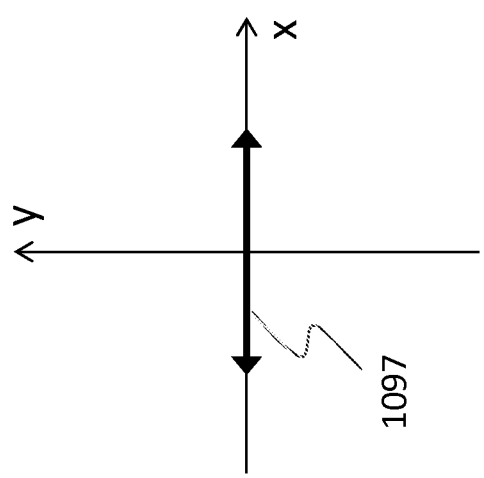

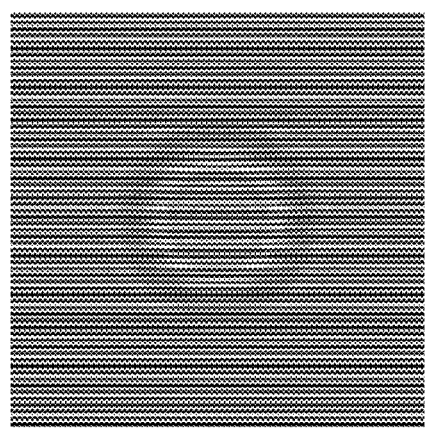
FIG. 21C
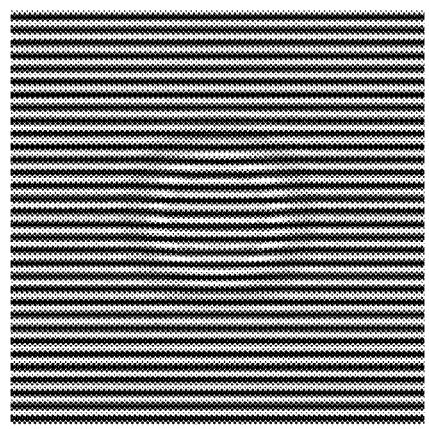
FIG. 21B
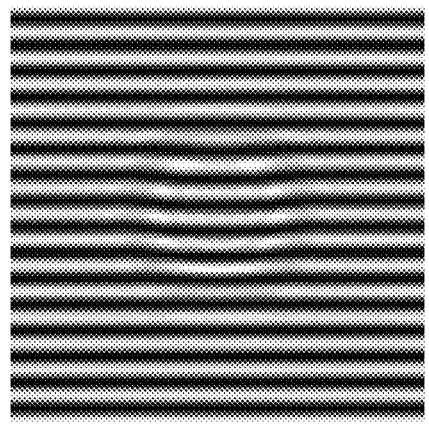
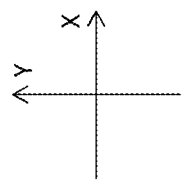
FIG. 21A

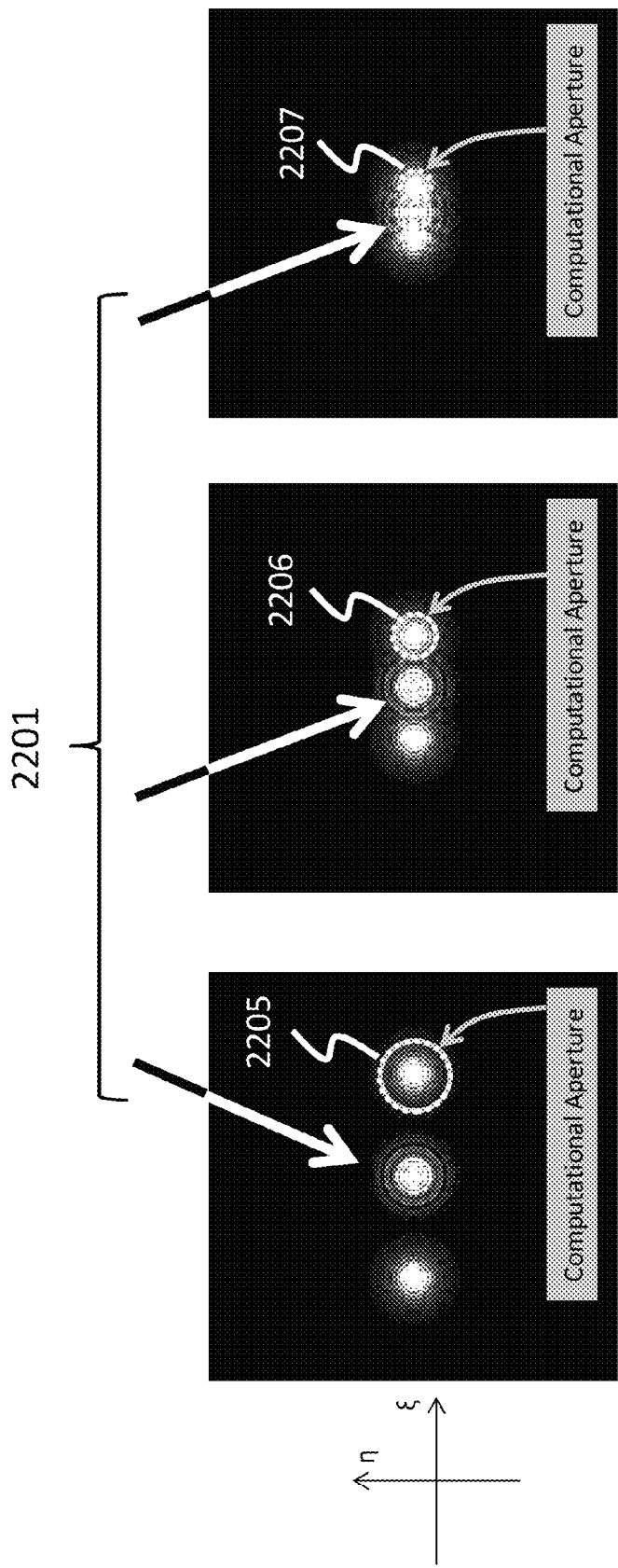

INTERFEROMETRIC METHOD AND DIGITAL HOLOGRAPHIC MICROSCOPE

BACKGROUND OF THE INVENTION

1. Field of the Invention

The present invention relates to an interferometric method for detecting information about a sample and a digital holographic microscope.

2. Description of the Related Art

There are two major methods for a digital holographic microscope which uses holograms to reconstruct an image of an object. One is a phase shift method (i.e., on-axis method), and the other is an off-axis method.

The on-axis method usually requires a plurality of holograms (e.g., four holograms) to observe the object from a direction and reconstruct the object image, because only one hologram cannot show whether the phase of the incident beam is delayed by the existence of the object.

Accordingly, the plurality of holograms are formed by using several reference beams whose phases are than different each other. In the on-axis method, the light intensity information of an image on the detector, which is obtained with each reference beam, is used for reconstructing the image of the object.

On the other hand, the off-axis method doesn't require such several holograms to reconstruct the image. In the off-axis method, an interference pattern formed by a reference beam and an object beam is used for reconstructing the image of the object.

The measurement time for the on-axis method can take, for example, four times longer than the off-axis method in light of the number of the holograms.

Since a plurality of holograms, which are obtained with various illumination angles to the object, are necessary to execute three-dimensional tomographic measurement of a phase object, the off-axis method may be selected in view of the measurement time.

Applying the off-axis method to the field of three dimensional measurements is a relatively new technique, and the technique is not matured yet. Accordingly, there is a need for an optical measurement system using the off-axis method for three dimensional measurements.

SUMMARY OF THE INVENTION

According to an aspect of the present invention, an interferometric method for detecting information about a sample includes: emitting a laser beam; splitting the laser beam into a reference beam and an object beam; transmitting the object beam through the sample in an incident angle; combining the reference beam with the object beam passed through the sample to form an interference pattern; detecting the interference pattern, and non-linearly (e.g., circularly or spirally) scanning the object beam in order to detect a plurality of interference patterns and to reconstruct a three-dimensional image of the sample.

According to another aspect of the present invention, an interferometric method for detecting information about a sample comprises emitting a laser beam; splitting the laser beam into a reference beam and an object beam; transmitting the object beam through the sample in an incident direction; combining the reference beam with the object beam passed through the sample to form an interference pattern; detecting the interference pattern, changing the incident direction of the object beam in order to detect a plurality of interference patterns; and changing a propagation direction of the reference beam so that each fringe pitch of the plurality of interference patterns is constant.

According to another aspect of the present invention, an interferometric method for detecting information about a sample comprises emitting a laser beam; generating a reference beam with a first polarization and an object beam with a second polarization from the laser beam; transmitting the object beam through the sample in an incident direction; combining the reference beam with the object beam passed through the sample to form an interference pattern; detecting the interference pattern, scanning the laser beam to change the incident direction of the object beam in order to detect a plurality of interference patterns.

According to another aspect of the present invention, a digital holographic microscope comprises a laser source configured to emit a laser beam; a beam splitter configured to split the laser beam into an object beam passing thorough a sample at an incident angle and a reference beam; a condenser configured to irradiate the sample with the object beam; an objective, the condenser and the object lens being arranged along an optical axis; a beam angle controller configured to rotate the object beam around the optical axis while maintaining the incident angle in order to form a plurality of interference patters; and a detector configured to detect the interference patterns.

According to another aspect of the present invention, an interferometric method for obtaining information about refractive index of a sample comprises preparing an object beam passing through a sample and a reference beam; forming an interference pattern with a fringe pitch by combining the object beam with the reference beam; detecting the interference pattern; and scanning the object beam to detect a plurality of interference patterns while maintaining the fringe pitch.

BRIEF DESCRIPTION OF THE DRAWINGS

FIG. 4 illustrates a range for the incident angle of the object beam.

FIGS. 21A, 21B, and 21C illustrate holograms.

FIGS. 22A, 22B, and 22C illustrate spatial frequency spectrums.

DESCRIPTION OF THE EMBODIMENTS

Embodiments according to the present invention will be described below with reference to the attached drawings.

First Embodiment

Circular Scan

Figure 1:
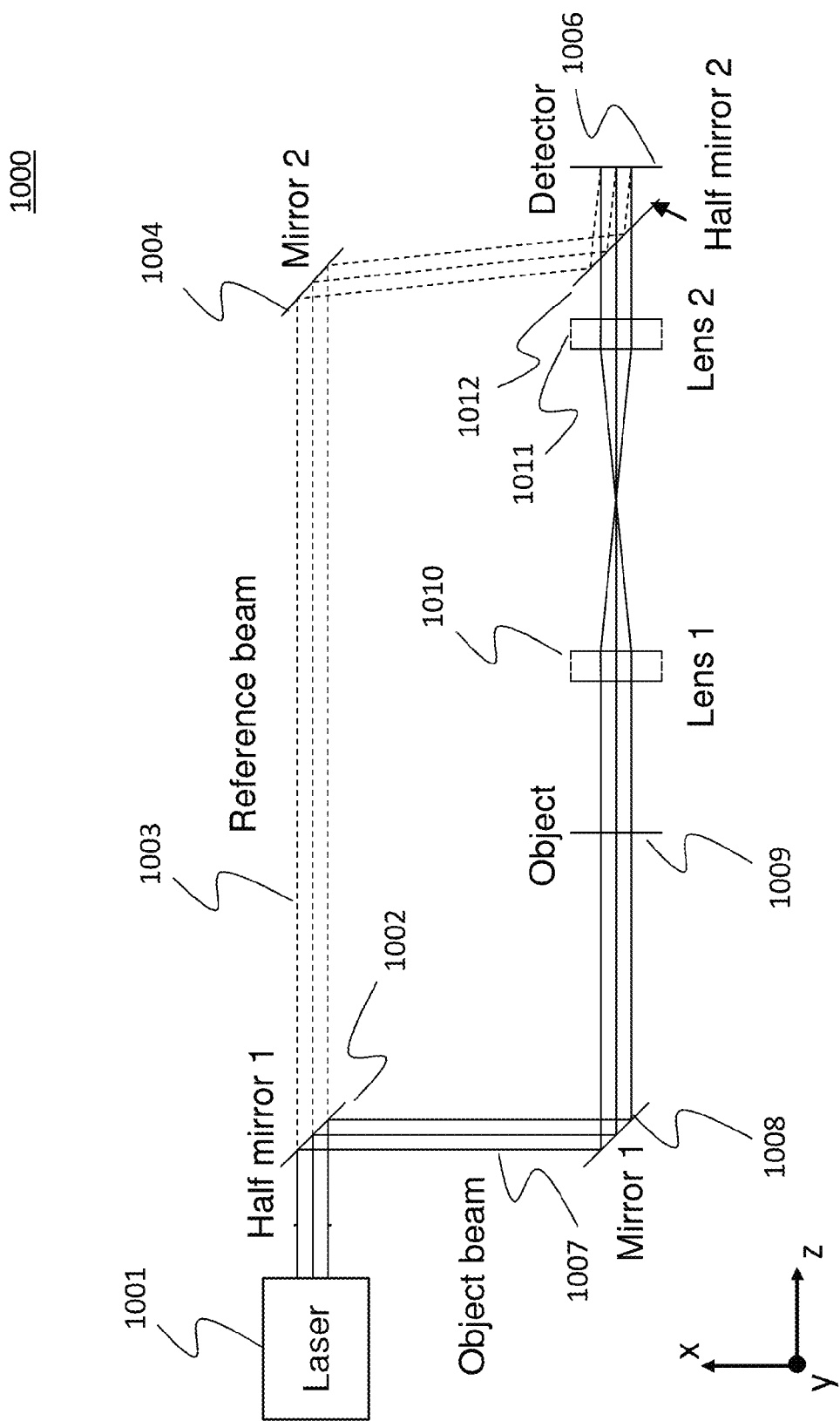
FIG. 1 illustrates a system for the off-axis method.

A system 1000 for performing the off-axis method is illustrated in FIG. 1. A display and a computer, which are not shown, can be used as the digital holographic microscope. A beam from a laser 1001 is split into a reference beam 1003 and an object beam 1007 by a half mirror 1002. The reference beam 1003 travels to the detector 1006 via a mirror 1004 and a half mirror 1012. As shown in FIG. 1, the object beam 1007 travels to an object (sample) 1009 via a mirror 1008. The object beam 1007 then travels through the object 1009 to the detector 1006 via two lenses 1010 and 1012, and a half mirror 1012. The object can be, for example, living or non-living cells, tissues, or organisms.

The phase information of the object 1009 is measured as an interference pattern (i.e., a fringe pattern) formed by the object beam 1007 and the reference beam 1003. To form the interference pattern on the detector 1006, the reference beam 1003 is not perfectly parallel to the object beam 1007. The detector will obtain information about the interference pattern as a digital hologram.

Figure 2:
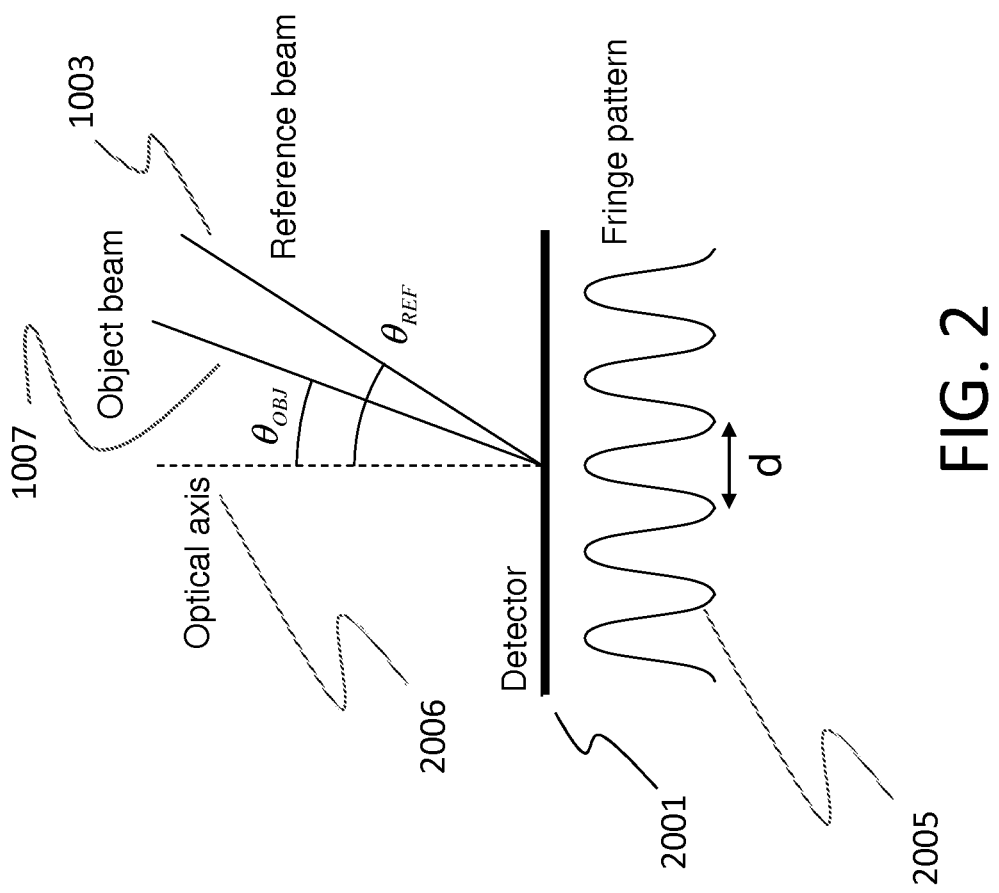
FIG. 2 is a chart illustrating the relationship between the object beam and the reference beam.

As shown in FIG. 2, the incident angles of two beams (the reference beam 1003 and the object beam 1007) to the detector 1006 are given by $\theta_{REF}$ and $\theta_{OBJ}$, respectively. The detector plane 2001 is perpendicular to the optical axis 2006 (dotted line in FIG. 2). Both of the angles $\theta_{OBJ}$ and $\theta_{REF}$ can be fixed during measurements. In a regular configuration, $\theta_{OBJ}=0$ and $\theta_{REF}$ is a few degrees (e.g., 0.6 degree) for the off-axis measurement. A fringe pitch d of the fringe pattern 2005 on the detector plane 2001 is related to the angles.

By the system 1000 for the off-axis method, the phase information of the object 1009 can be obtained by a single measurement. Hologram data obtained by the detector 1006 will be stored in a memory or data storage (not shown). An image reconstruction based on the hologram data can be conducted computationally, which is so-called digital holographic microscopy.

Three-dimensional tomographic measurement of a phase object based on the digital holographic microscopy can be executed by using the off-axis method. Multiple holograms obtained with different illumination angles will be used for a 3D reconstructed image by computation.

Figure 3:
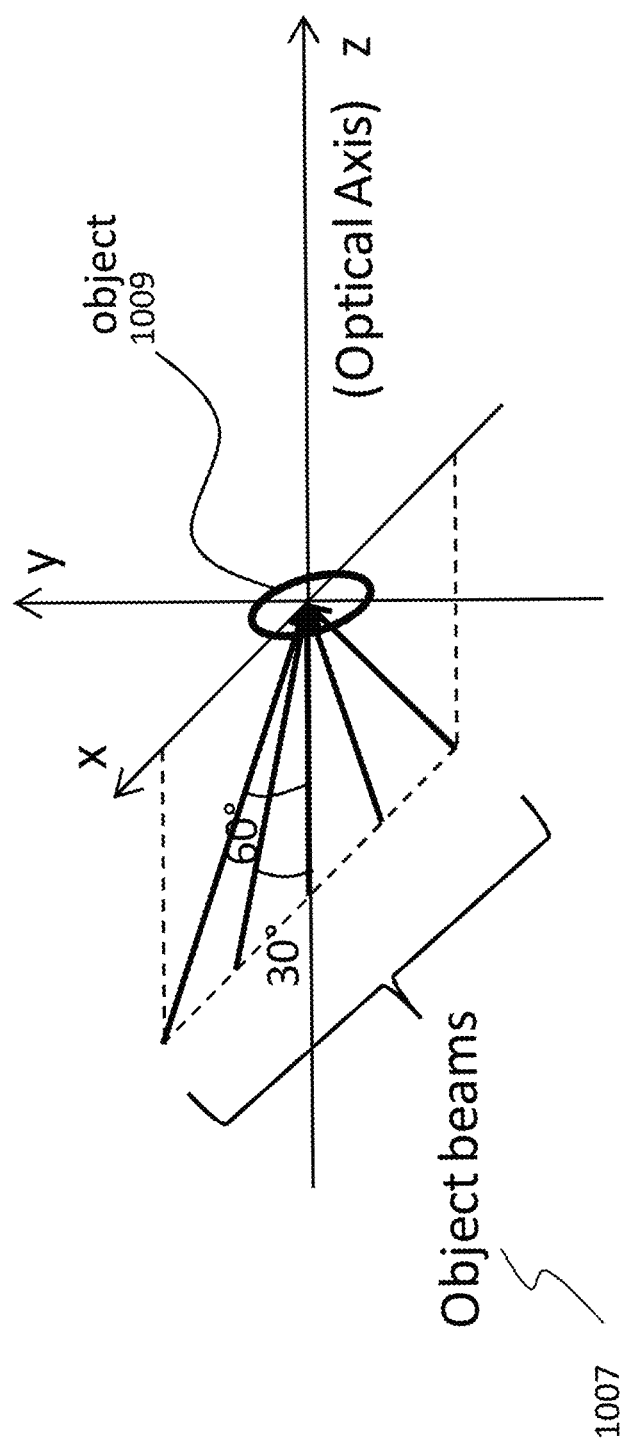
FIG. 3 is a chart illustrating a linear scan of the object beam.
Figure 5B:
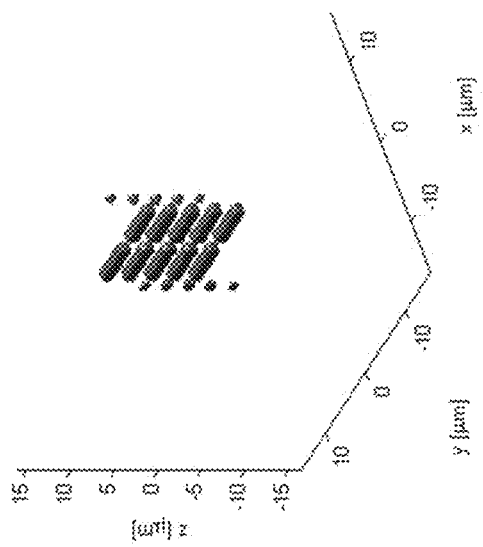
FIG. 5B illustrates a reconstructed image of the bar structure by using the linear scanning method.
Figure 5A:
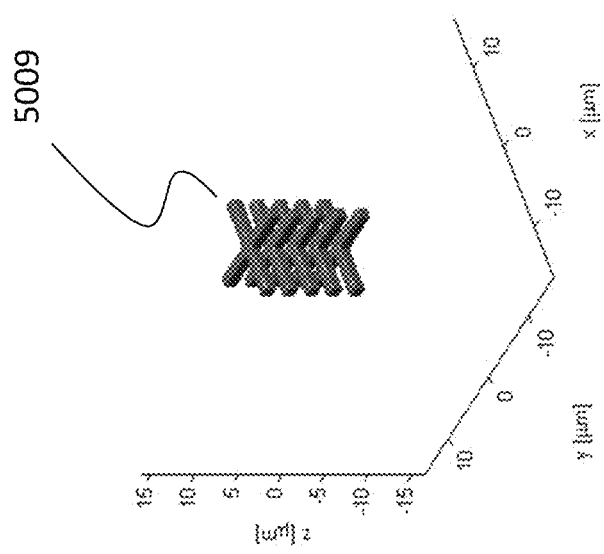
FIG. 5A illustrates a bar structure as a sample.

To obtain the multiple holograms, the object beam 1007 might be linearly scanned along the x-axis as illustrated in FIG. 3. The range for the incident angle of the object beam 1007 is illustrated in FIG. 4. The arrow 1097 means the scanning track. However, when the shape of the sample as the object is a bar structure 5009 as illustrated in FIG. 5A, the axial resolution for the bar structure 5009 along the x-axis is not as high as the one along the y-axis. The pitch of this bar structure in FIG. 5A is 2.54 µm, and the wavelength is 0.543 µm. The reconstructed image obtained by the linear scan is illustrated in FIG. 5B.

The reconstructed image by the linear scan includes 100 angles between ±60 degrees. The theoretical method to calculate this image will be explained later. The bar structure in the image of FIG. 5B along y-axis is reconstructed well, but the other one along x-axis is not sufficiently resolved.

Fringe Pitch

When the wavelength of the beams is λ, the pitch d of the fringe pattern created on the detector without an object is given by the following equation (1).

$$d = \frac{\lambda}{|\sin \theta_{REF} - \sin \theta_{OBJ}|} \tag{1}$$

$\theta_{OBJ}$ and $\theta_{REF}$ are defined as illustrated in FIG. 2. The fringe pattern can be modulated by the existence of a phase object which has a phase distribution. The value of the pitch d should be minimized to get holograms with high resolution because the resolution would be decided by the pitch d, when the pitch d is bigger than a diffraction-limited spot decided by 0.61*λ/NA.

However, the smallest value of the pitch d is limited due to the pixel pitch of the detector 1006 (e.g., CMOS or CCD). Therefore, there is an optimum value of d that is determined according to the detector property.

When an illumination angle to the object is changed in the x-y plane, the fringe pitch is also varied according to the illumination angle.

By changing the angle of the mirror 1008 in the x-y plane for the object beam 1007, the illumination angle and an angle ($\theta_{OBJ}$) of the object beam on the detector 1006 are changed accordingly.

In the off-axis technique, when the beam angle illuminating the object is changed during the observation, the fringe pitch formed on the detector 1006 is also changed with the change of the angle ($\theta_{OBJ}$).

Resolution of the detector or a field of view (hereinafter, FOV) can be affected by the change of the fringe pitch. Now we assume the situation that the required resolution is 0.5 μm and the number of the pixels is 1000. Since the line width of fringes should not be larger than the resolution, we can decide 0.5 μm as the fringe width, which is a half of the pitch width. At least three pixels are required to resolve one fringe, so four pixels may be optimum, so one fringe width, 0.5 μm, corresponds to four pixels.

This condition can be obtained by changing the magnification of the objective lens, or an inserting a focal system in front of the detector. Then, FOV (field of view) is 125(=(0.5/4)*1000) μm, and this is satisfied by the first illumination angle. Next, think about the second illumination angle. If the fringe pitch becomes double, 1 μm, the resolution is also double. Then, if the pitch for the second angle can be half by changing the magnification to satisfy the resolution, the pitch for the first angle is also half, 0.25 μm, and then FOV is also half, 62.5(=(0.25/4)*1000)μm. Therefore, the ratio between the fringe pitches for the first angle and the second angle is 2, the resolution will be double, or the FOV will be half.

A novel configuration with a circular scan for a tomographic digital holographic microscopy will be explained below.

The configuration can have an ability to obtain symmetric reconstructed images along x and y axes. Therefore, the bar structures along both x and y-axes can be reconstructed well simultaneously with the same number of angles, e.g. 100 angles.

Figure 6:
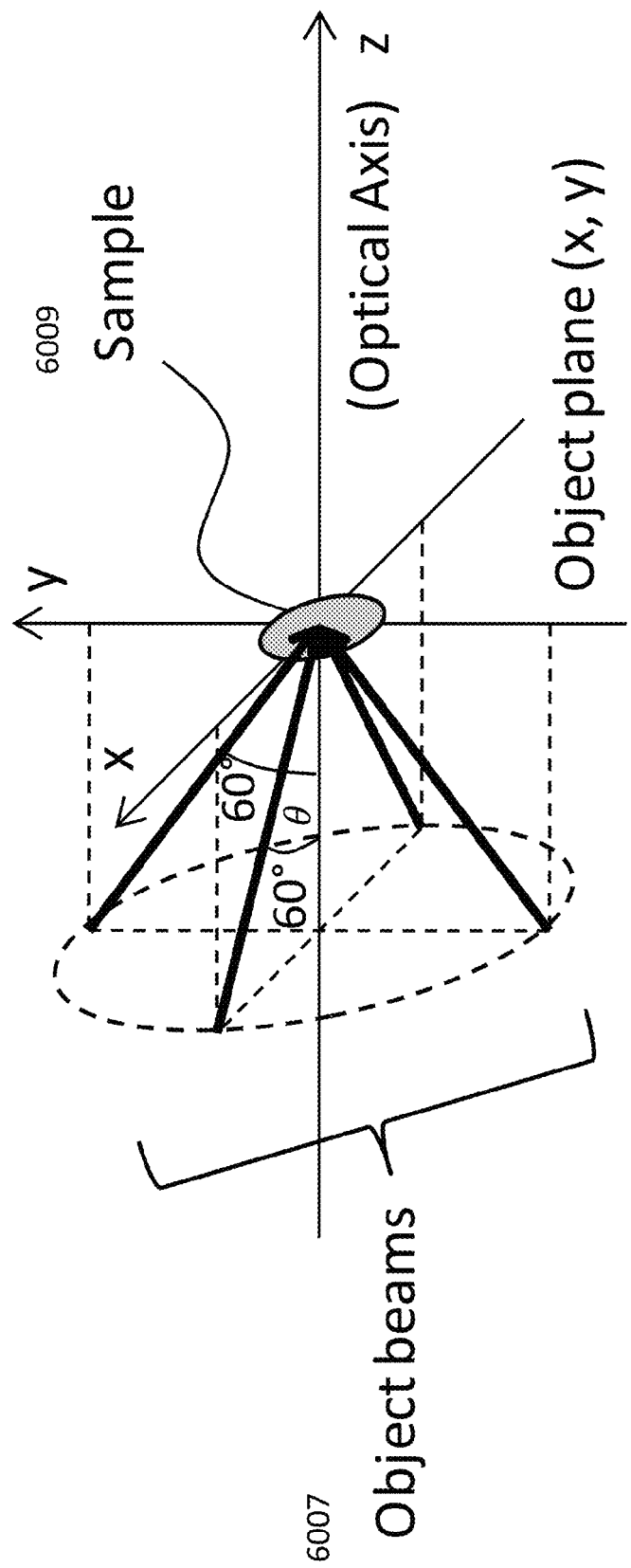
FIG. 6 illustrates directions of the object beam to the sample.

A configuration of object beams applying a sample 6009 is illustrated in FIG. 6. The configuration includes four object beams 6007 as an example. These beams 6007 can be applied to the sample 6009 one by one. For a practical use, the angle number of the object beams might be more than four, for example, the number may be 100, but here only a few beams are used for ease of viewing the exemplary figure. This scan method can be called as circular scan.

Figure 7:
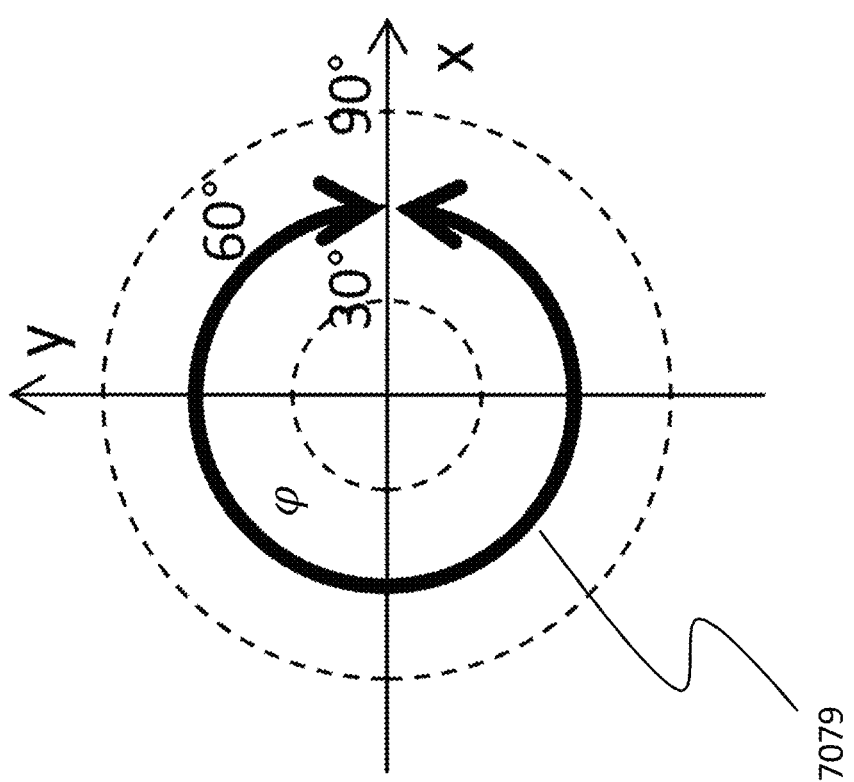
FIG. 7 illustrates an incident angle of the object beam in a circular scan.

The range for the incident angle (illumination angle) of the object beam 6007 in the circular scan is illustrated in FIG. 7. The circle with the arrow 7079 in FIG. 7 is indicating the condition in FIG. 6.

If the circular scan is expressed with polar coordinates (θ, φ), θ can always be 60° and φ can be from 0° to 360° in FIG. 7. θ is the illumination angle to the optical axis. φ is a rotation angle.

The 60° of the θ is one example. However θ can be another angle, as long as the angle is not too small or too big. The angle θ may be selected in the range between 25° and 75°, for example.

With a too small angle (e.g., 5°), an axial resolution would become low. With a too big angle (e.g., 85°), the object beam may not be able to go through an aperture of an objective lens 1810 in FIG. 8. The aperture will be explained later.

Figure 8:
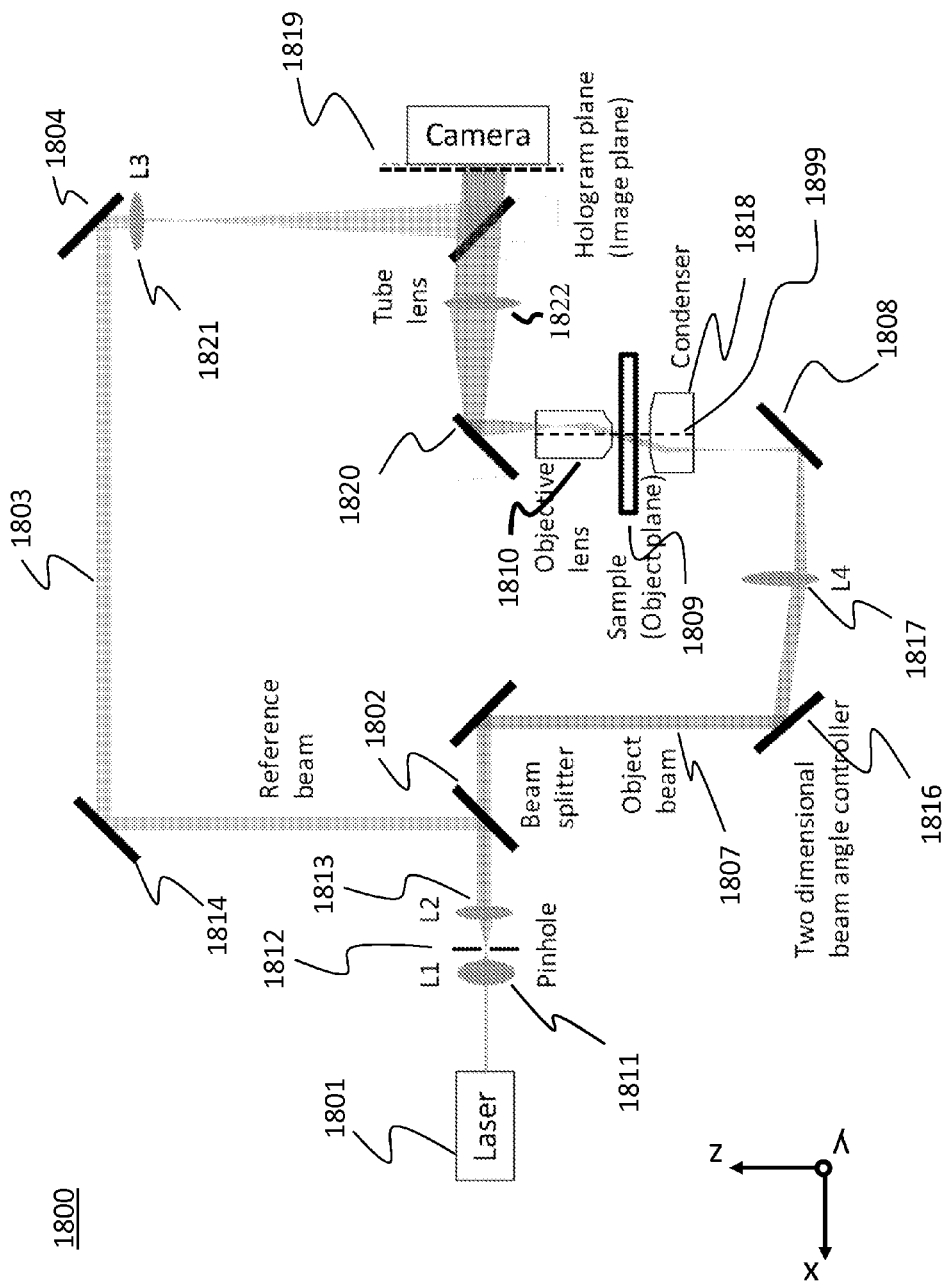
FIG. 8 illustrates a system for interferometric method.

The system configuration for the digital holographic microscopy is illustrated in FIG. 8. A He—Ne laser beam (λ=543 nm) from a laser source 1801 is divided into object beam 1807 and reference beam 1803 by a beam splitter 1802. The lens L1 1811, a member 1812 with a pinhole, and a lens L2 1813 are used. Mirrors 1804, 1808, 1814, and 1820 are used in the system.

As to the object beam 1807, the beam angle is two-dimensionally controlled by a two-dimensional beam angle controller 1816. A lens L4 1817 is located at a position of the focal length of the lens L4 1817 from the beam angle controller 1816. A condenser 1818 is located at a position of the sum of the L4 1817 focal length and a focal length of the condenser lens from L4 1817, so that the beam in the sample is collimated, and also the sample 1809 is located at a conjugate plane with the beam angle controller 1816. Then, the object beam 1807 through the sample 1809 is collected by the objective lens 1810. The image of the object is formed on the image plane 1819 via a tube lens 1822. The obtained hologram is related to refractive index information of the sample to be used for 3D imaging.

If the length between the objective lens 1810 and the tube lens 1822 is shorter than the sum of the focal length for these lenses, 1810 and 1822, then the beam is divergent in the hologram plane 1819.

In a path of the reference beam 1803, a lens L3 1821 is located at the position, so that a wavefront of a reference beam matches with a wavefront of the object beam wave-front caused by the divergence.

Figure 9C:
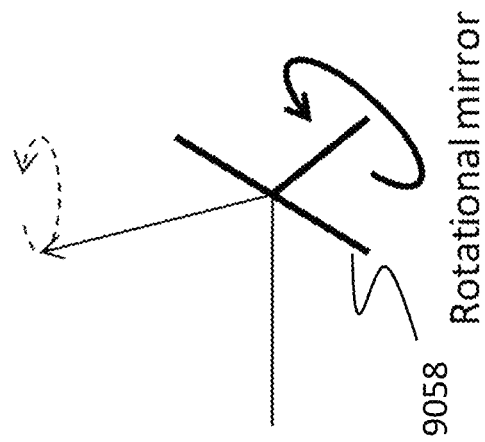
FIGS. 9A, 9B, and 9C illustrate beam angle controllers.
Figure 9B:
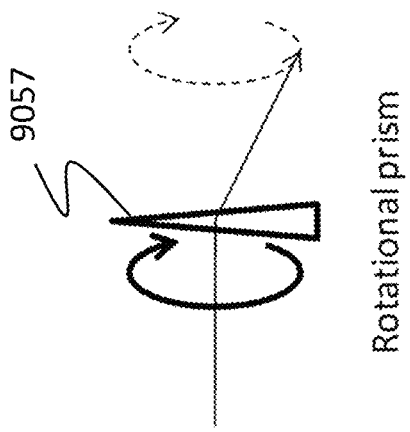
Figure 9A:
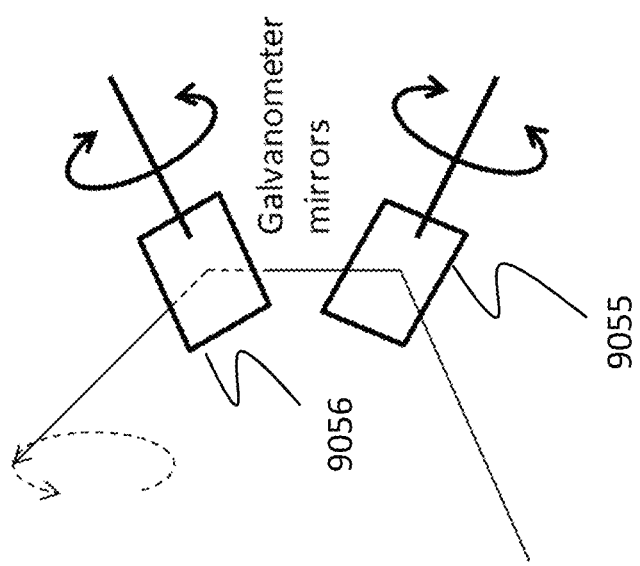

A component for the two-dimensional beam angle controller 1816 can be exemplary selected from one of the units illustrated in FIGS. 9A, 9B, and 9C.

In FIG. 9A, the unit uses two Galvanometer mirrors. The first mirror 9055 can control a horizontal angle, and the second one 9056 can control a vertical angle. By combination with two angles, the circular scan can be executed. Units in FIGS. 9B and 9C are the controller with a rotational prism 9057 and mirror 9058 respectively. The rotations of them can directly generate the circular scan. By using the beam angle controller, the incident angle of the object beam can rotate around the optical axis 1899 between the objective lens 1810 and the condenser 1818 while maintaining an angle between the incident angle of the object beam and the optical axis.

There are commercially available dual Galvanometer mirrors as illustrated in FIG. 9A. The beam controller 1816 would need to be located at the conjugate plane with the sample. However, the two mirrors 9055 and 9056 may not be precisely at the conjugate plane simultaneously except for making system complicated, e.g., setting a relay lens system between two mirrors. If the first or second mirror is located at the conjugate plane, the position of the incident beam applied to the sample is shifted. The shift amount can be minimized when the midpoint of two mirrors is conjugate with the sample.

Under the condition that focal lengths for L4 1817 and the condenser 1818 are 100 mm and 9 mm respectively and a distance between two mirrors is 13 mm, the shift amount is 0.16 mm against 0.9 mm of a diameter of the object beam and 0.24 mm as the FOV. The beam diameter of the object beam on the beam angle controller is 10 mm. The FOV comes from a microscope specification with 100× magnification. The beam diameter is within sum of the shift amount and the FOV, so the shift amount is within an acceptable range. With this consideration, the dual Galvanometer mirrors can be used as the two-dimensional beam angle controller 1816.

Figure 10:
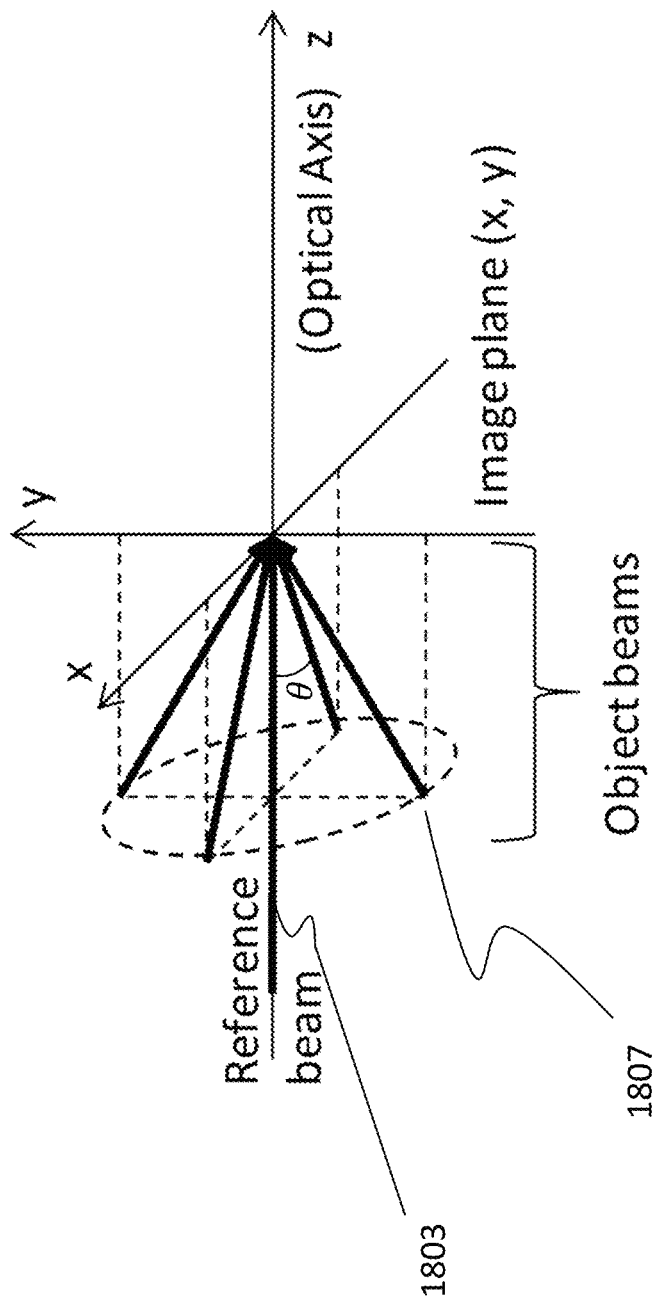
FIG. 10 illustrates the object and reference beams on the image plane of the detector.

The object and reference beams on the image plane are illustrated in FIG. 10. This figure includes four positions of the object beam 1807 as an example corresponding to the positions of the beam in FIG. 6. Also, this figure includes the reference beam 1803, which is normal to the image plane.

The reference beam 1803 is normal to the image plane (x-y plane), and an incident angle δ of the object beam 1807 to the reference beam 1803, which is along the optical axis, is fixed. This angle δ can be calculated by the following equation (2). M is a magnification of a combination of objective and tube lenses. $n_{oil}$ is a refractive index of an immersion oil for the objective lens. 60° is the angle in FIG. 7.

$$\theta = \sin^{-1}\left[\frac{n_{oil}\sin 60°}{M}\right] \quad (2)$$

When the θ is fixed, the angle between object and reference beams can always be the same while circular scanning.

Fringe patterns are generated in the image plane by the two beams, and they can be stored as holograms. Since the angle between two beams is always the same, the fringe pitch can be substantially constant. Theoretically the fringe pitch can be constant, but practically the fringe pitch can be changed within a range of ±5% of the pitch. The change may be caused due to an experimental alignment error. In this embodiment, when the fringe pitch substantially maintains a value, the change of the pitch is within the range of ±5% of the pitch width.

Figure 11:
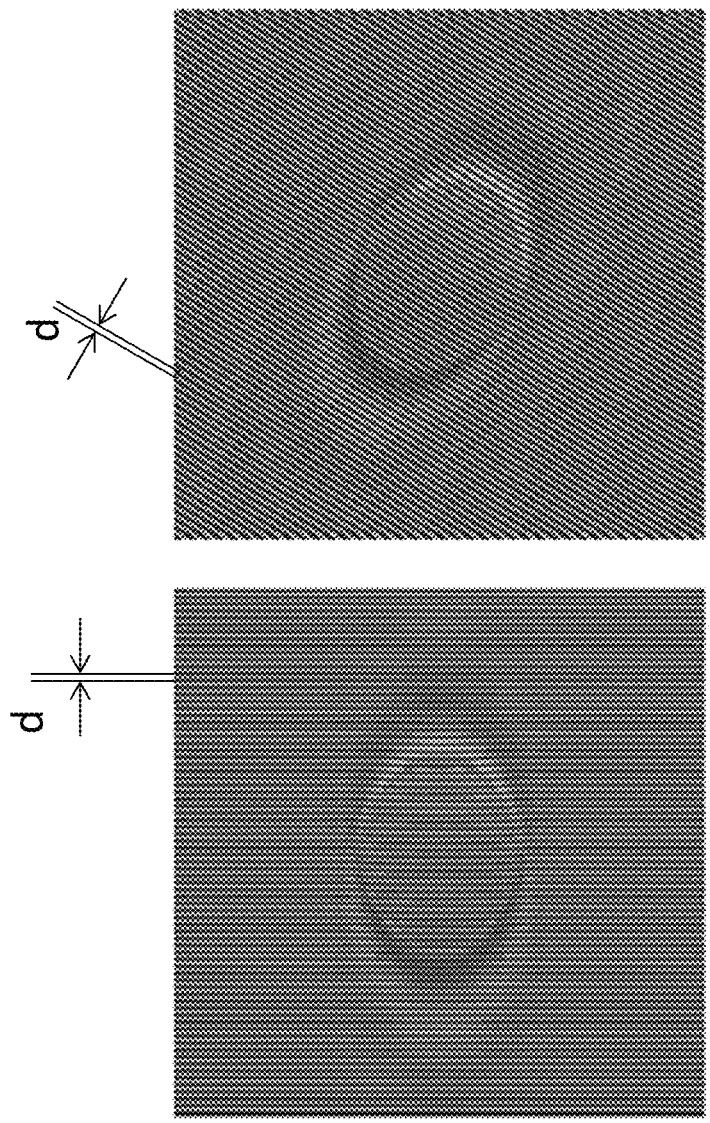
FIGS. 11A and 11B illustrate synthesized holograms.

Synthesized holograms with φ (0° and 30°) are illustrated in FIGS. 11A and 11B, respectively. The sample is a 10 μm bead in oil. The refractive indices for a bead and oil are 1.588 and 1.559 respectively. The pitches for both angles are the same. The fringe pitch d of FIG. 11A is the same as a fringe pitch of FIG. 11B.

Then, the fixed fringe pitch will not make the resolution and FOV degraded because the optimized fringe pitch for the resolution and FOV can be used for all illumination angles.

Figure 12:
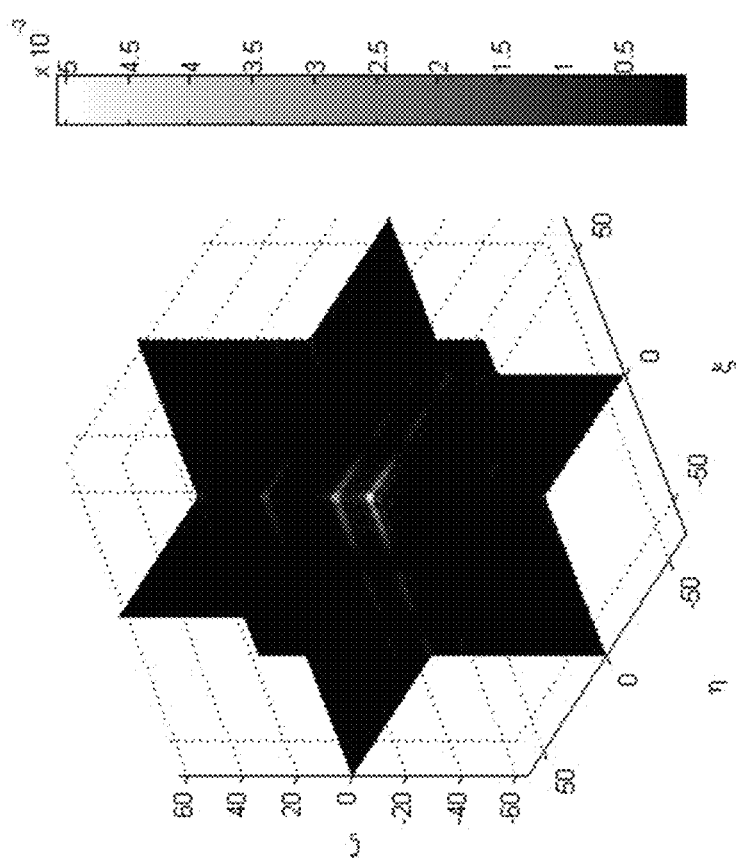
FIG. 12 illustrates a cross section of a spatial frequency spectrum of the bar structure calculated by Fast Fourier Transform (FFT).

The ability of the circular scan system will be estimated. The test object is the same as FIG. 5A. A cross section for a spatial frequency spectrum of the test object calculated by FFT) is shown in FIG. 12. The spectrum can be obtained by the off-axis method. By the certain incident angle (illumination angle), some portions of this spectrum can be observed. The axes ξ, η and ζ in a Fourier space correspond to x, y and z in a real space, and the color bar in the right hand side shows the amount of amplitude of the spectrum.

Figure 13B:
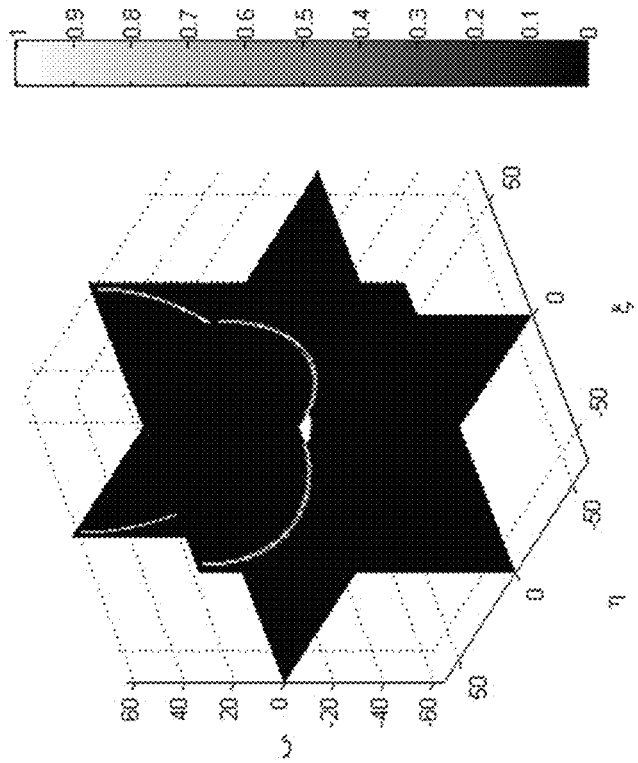
FIG. 13B illustrates a cross section of the 3D spherical shell for a single object beam angle that is along the optical axis.
Figure 13A:
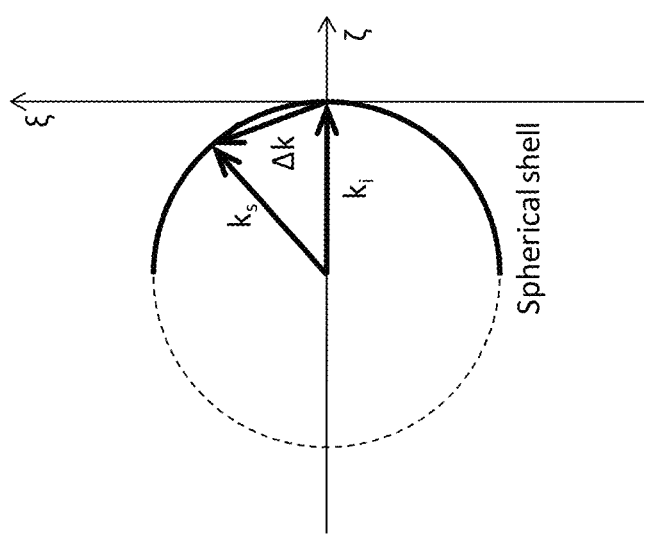
FIG. 13A illustrates a spherical shell for a single object beam angle that is along the optical axis.

FIG. 13A shows an incident wave vector ($k_i$), an a wave vector scattered by the object ($k_s$), and a difference between them ($\Delta k = k_s - k_i$). Since general objects can't change a wavelength of the incident beam, the length of $k_i$ and $k_s$ are the same. Therefore, Δk will be on the surface of a sphere. The system is a transmission mode, so the angle between $k_i$ and $k_s$ is less than 90°, and then the sphere is actually a hemisphere. This hemisphere is called as a spherical shell herein.

Figure 13D:
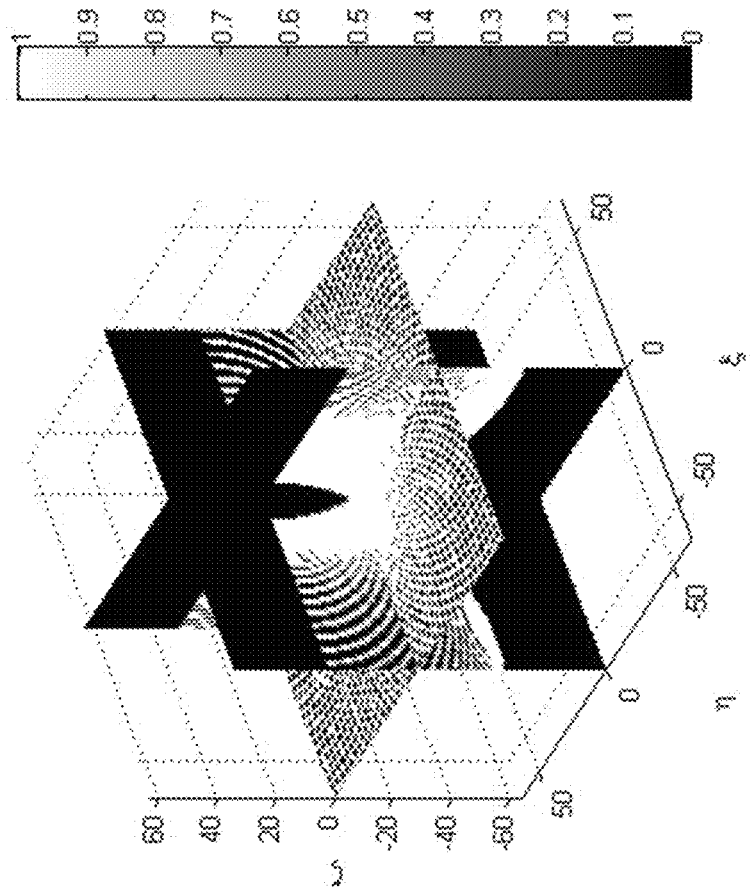
FIG. 13D illustrates spherical shells for the circular scan with 100 angles.
Figure 13C:
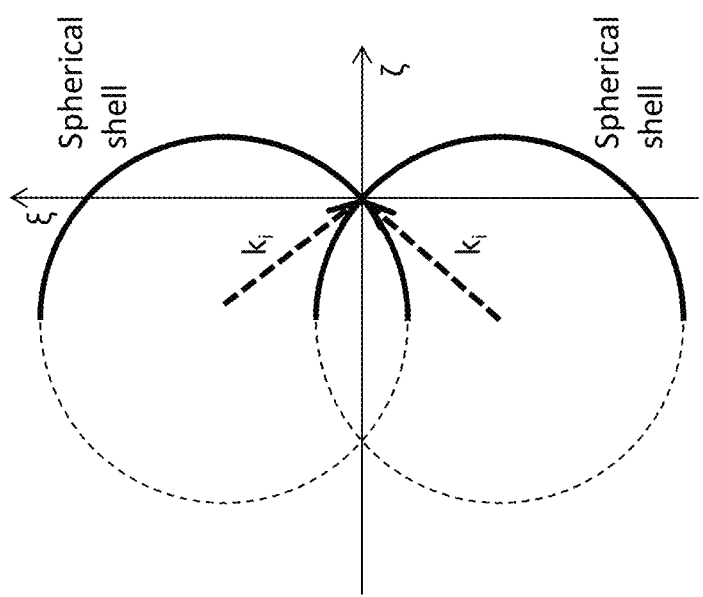
FIG. 13C illustrates two angles of the circular scan.
Figure 13E:
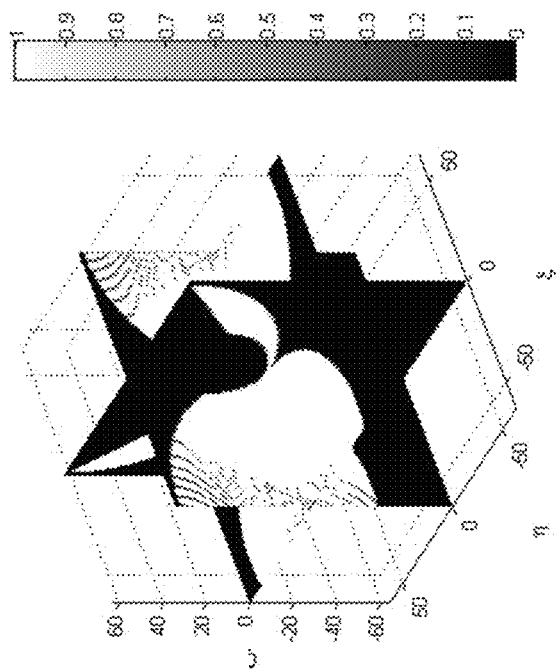
FIG. 13E illustrates spherical shells for the linear scan with 100 angles.

FIG. 13A shows a case of that the incident beam is along the optical axis, which means (θ, φ)=(0, 0). FIG. 13A is a 2D image, but FIG. 13B is a 3D image of the spherical shell. FIG. 13B shows the cross section 3D spherical shell of FIG. 13A. With the incident beam along the optical axis, only the spectrum on the spherical shell FIG. 13B can be observed. In a numerical method, a reconstructed image can be calculated by IFFT of the product of FIG. 12 and FIG. 13B. FIG. 13C shows two spherical shells corresponding to two incident angles of the circular scan. $k_i$ is tilted according to the incident angle. FIG. 13D shows spherical shells for the circular scan with 100 angles (θ, φ)=(60°, from 0° to 360°). On the other hand, FIG. 13E shows spherical shells for the linear scan with 100 angles (θ, φ)=(from −60° to 60°, 0°). FIG. 5B is a calculation result of FFT of the production of FIG. 12 and FIG. 13E.

FIG. 12 shows the 3D spectrum of the object illustrated in FIG. 5A, calculated by FFT (Fast Fourier Transform). If IFFT (Inverse Fast Fourier Transform) is applied on FIG. 12, the same image as FIG. 5A can be obtained except for minor numerical errors. Then, by multiplying the spherical shells, e.g., FIG. 13D, on FIG. 12 before applying IFFT, the image corresponding to the scanning method can be obtained.

Figure 14:
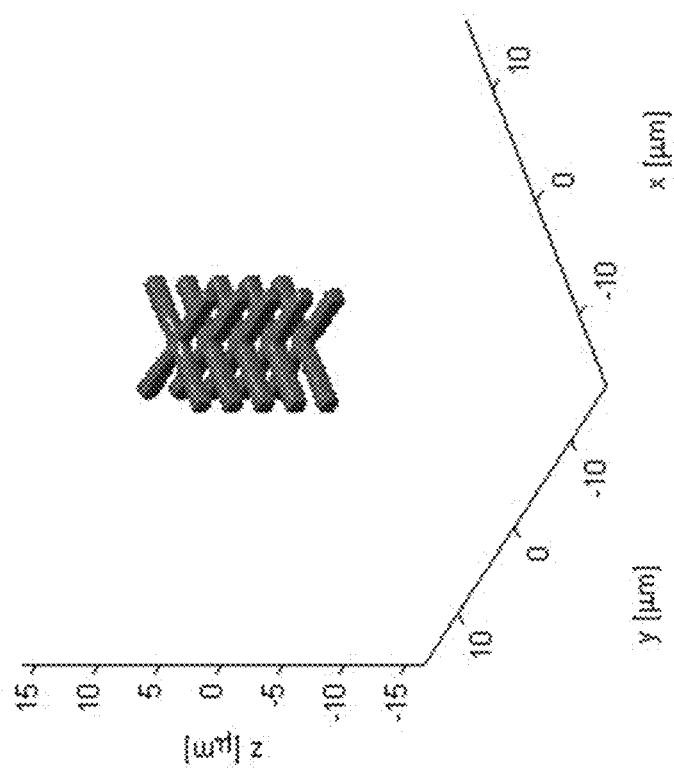
FIG. 14 illustrates a reconstructed image by the circular scan with 100 angles.

FIG. 14 shows the reconstructed image by the circular scan with 100 angles. This image is calculated by FFT of the production of FIGS. 12 and 13D. This image is symmetric for x and y-axes. The bar structure along both x and y-axes are reconstructed well.

In this example, φ was from 0° to 360°, but this range could be shortened. For example, even if a scan range is half, which means φ is from 0° to 180°, a relatively reasonable reconstructed image can be obtained.

Also, the θ, which is the illumination angle, doesn't need to be fixed precisely. The 6 can be changed, for example, from 60° to 50° during scanning, but a fluctuation of the angle θ might make the axial resolution degraded.

Figure 15:
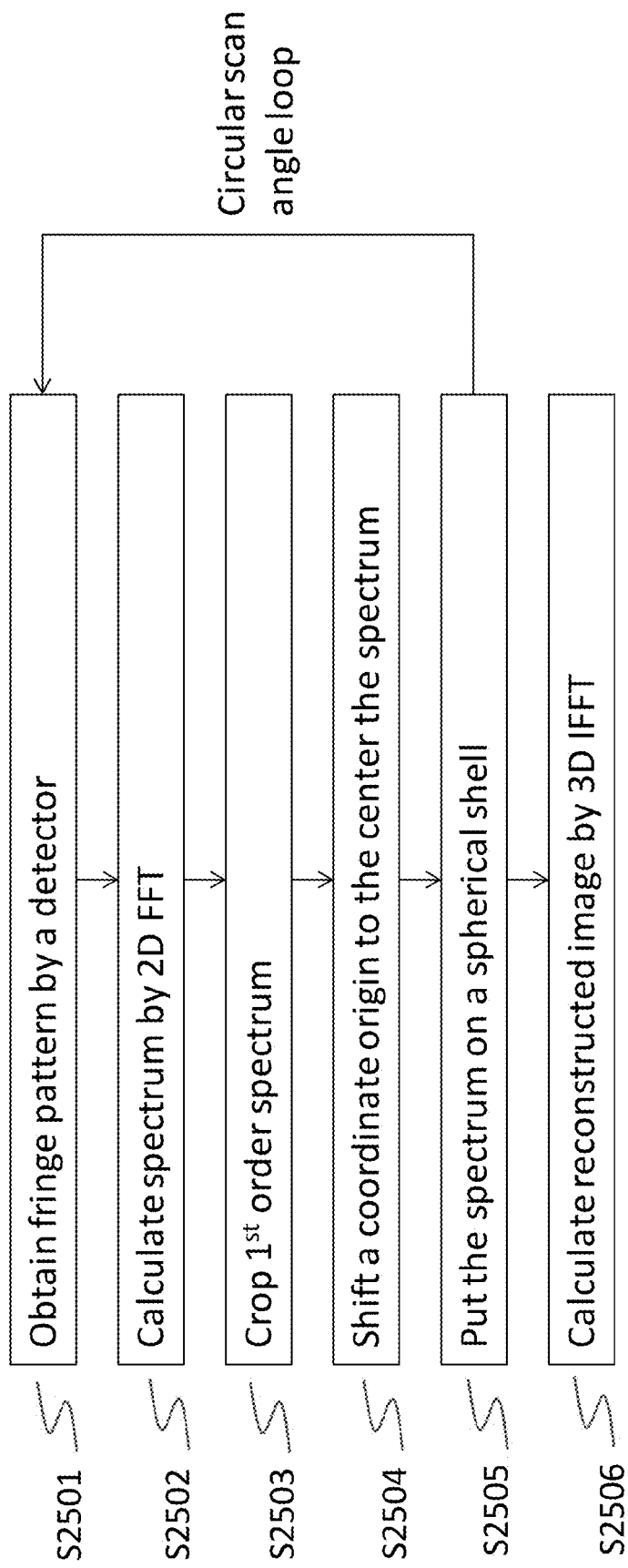
FIG. 15 illustrates a flowchart for a 3D reconstructed method.

Here, a reconstruction process is described from the view point of software. FIG. 15 shows a flowchart for a 3D reconstruction algorithm.

A fringe pattern is obtained by a detector for a certain scanning angle in S2501. In S2502, a spatial frequency spectrum is obtained by a calculation based on a numerical 2D FFT. The 1st order spectrum is cropped (selectively collected) by using a computational aperture according to the object beam angle in S2503.

The light intensity on the detector is expressed as:

$$|E_O(x,y)+E_R(x,y)|^2 = |E_O(x,y)|^2 + |E_R(x,y)|^2 + E_O(x,y)E_R^*(x,y) + E_O^*(x,y)E_R(x,y) \quad (3)$$

$E_O(x, y)$ and $E_R(x, y)$ are electric fields for the object and reference beams respectively. The first and second terms correspond to 0th order light. The third term corresponds to +1st order light, and the fourth term corresponds to −1st order light.

The third term can be re-written as follows. We can't see a phase itself because a light propagate with a very high speed, but we can see a phase difference. $\phi_O(x, y) - \phi_R$ in the following equation (4) means the phase difference.

$$\begin{aligned} E_O(x, y)E_R^*(x, y) &= |E_O(x, y)| \exp[i\phi_O(x, y)] \cdot |E_R(x, y)| \exp[-i\phi_R] \quad (4) \\ &= |E_O(x, y)| \cdot |E_R(x, y)| \exp[i(\phi_O(x, y) - \phi_R)] \\ &\propto |E_O(x, y)| \exp[i(\phi_O(x, y) - \phi_R)] \end{aligned}$$

The +1st order light can be picked up by using a computational aperture, and Fourier transform of the +1st order light corresponds to the equation above. Thus, phase distribution can be reconstructed.

Since the 1st order peak position is shifted according to the illumination beam angle φ, the aperture needs to be shifted. If the circular scan used, the aperture is shifted circularly.

In S2504, the origin for a coordinate is shifted to the center of the spectrum to remove fringe patterns. In S2505, the cropped spectrum is put on a spherical shell according to the object beam angle φ.

These procedures will be executed for all scanning angles φ, and calculate spherical shells such as FIG. 13D. Then, finally, a reconstructed image is calculated by numerical 3D IFFT in S2506.

Figure 16:
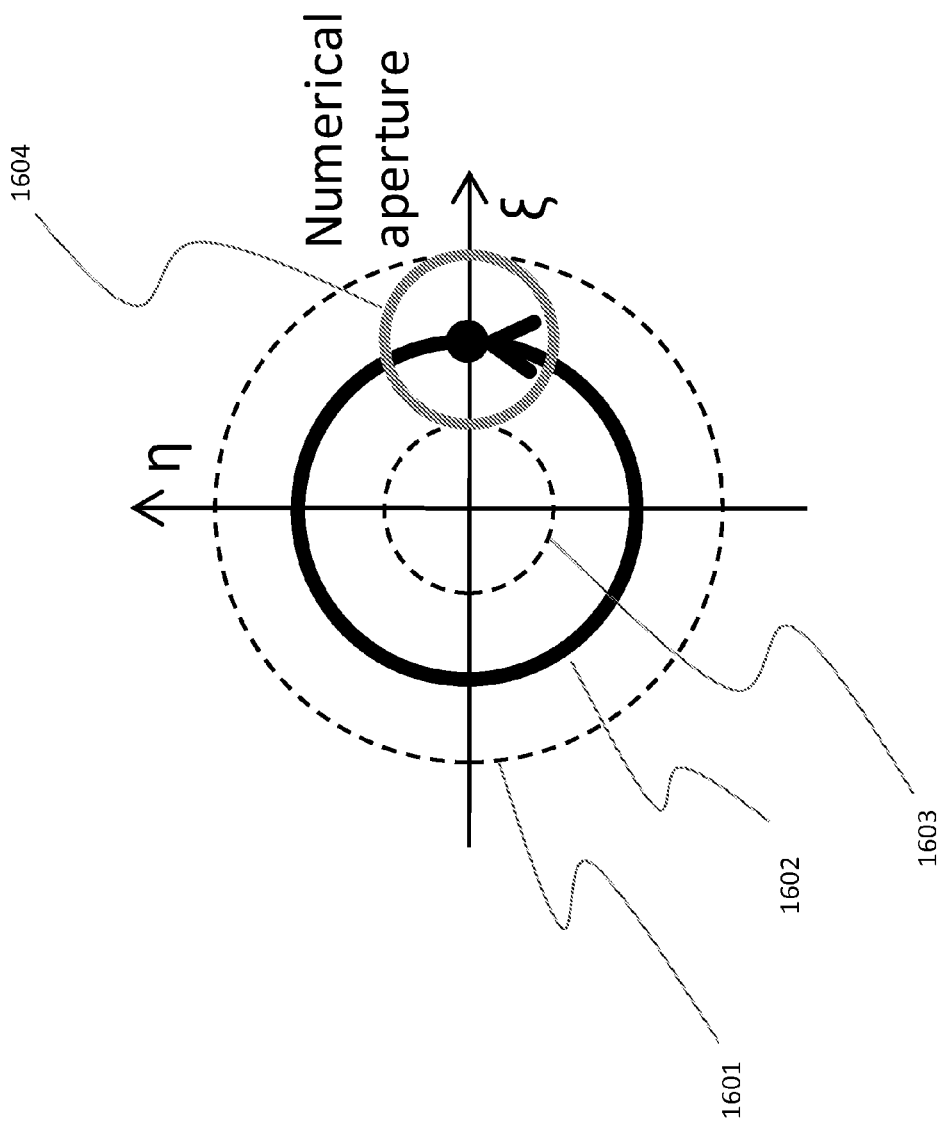
FIG. 16 illustrates a computational aperture to crop the $1^{st}$ order spectrum.

FIG. 16 illustrates the computational aperture 1604 to crop the 1st order spectrum obtained by the circular scan. The axes ξ and η in a Fourier space shows x and y in a real space. 1601, 1602 and 1603 show 90 degree, 60 degree and 30 degree as θ respectively.

The aperture 1604 is used in S2503 of FIG. 15. This position corresponds to the object beam angle, FIG. 7.

Figure 17:
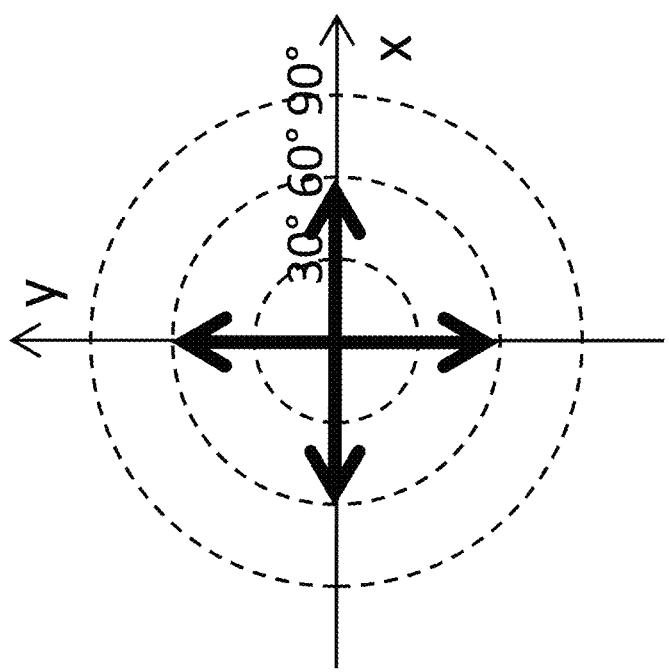
FIG. 17 illustrates a range for the incident angle of the object beam.

FIG. 17 shows another range for the incident angle of the object beam, in order to cover Fourier space with spherical shells. This scan is a combination with a horizontally linear scan and a vertically linear scan. Then, this scanning method can be called as a crossed scan.

Figure 18:
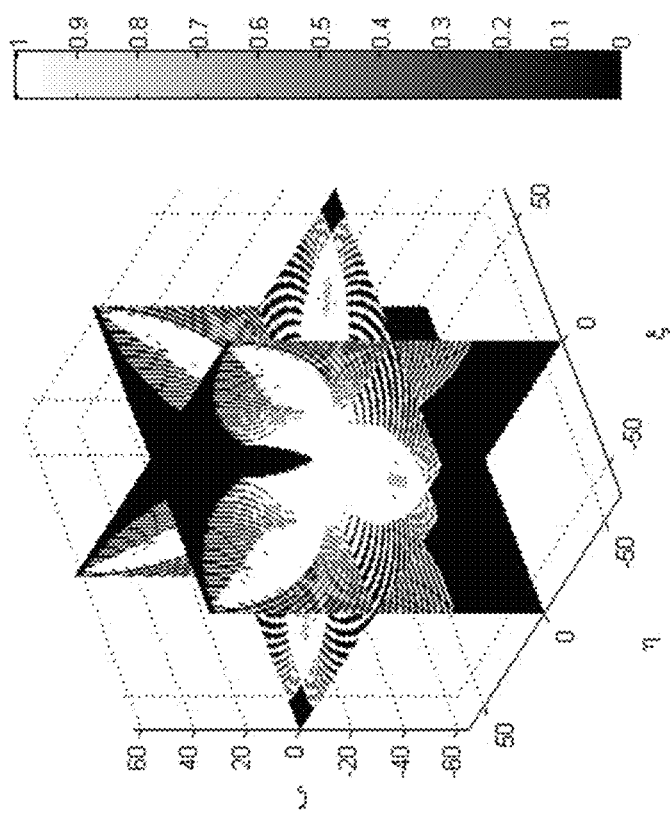
FIG. 18 illustrates cross sections of spherical shells for the dual linear scan with 200 kinds of angles.

FIG. 18 shows spherical shells for the crossed scan with 100 angles (θ, φ)=(from −60° to 60°, 0°) and (from −60° to 60°, 90°), which means 50 angles along the horizontal direction and 50 angles along the vertical direction.

Figure 19:
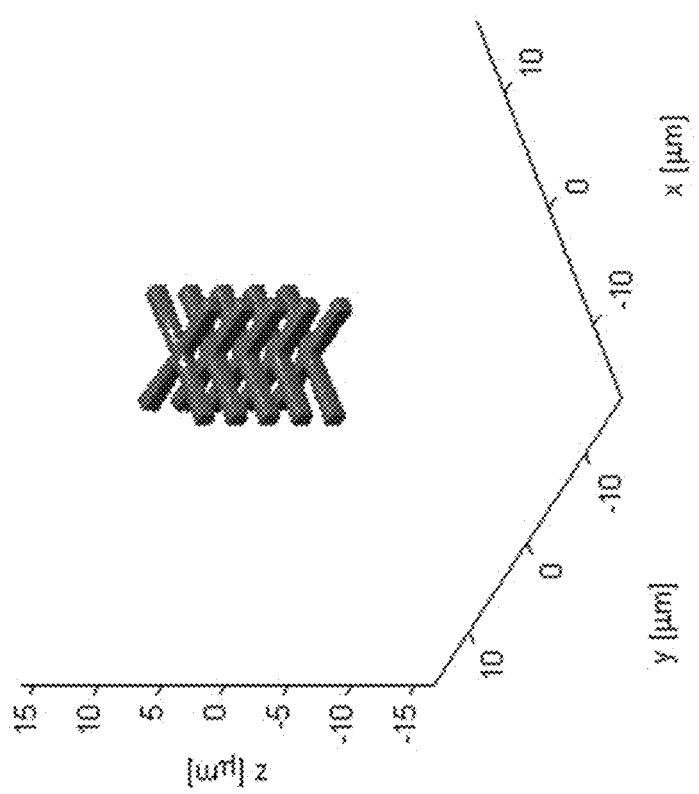
FIG. 19 illustrates a reconstructed image by using a crossed scan.

FIG. 19 shows the reconstructed image by the crossed scan with 100 angles. This image is calculated by FFT of the production of FIGS. 12 and 18. This image is also symmetric for x and y-axes. The bar structure along both x and y-axes can be reconstructed.

Second Embodiment

Spiral Scan

The following configuration in this embodiment is based on the off-axis method.

Figure 20:
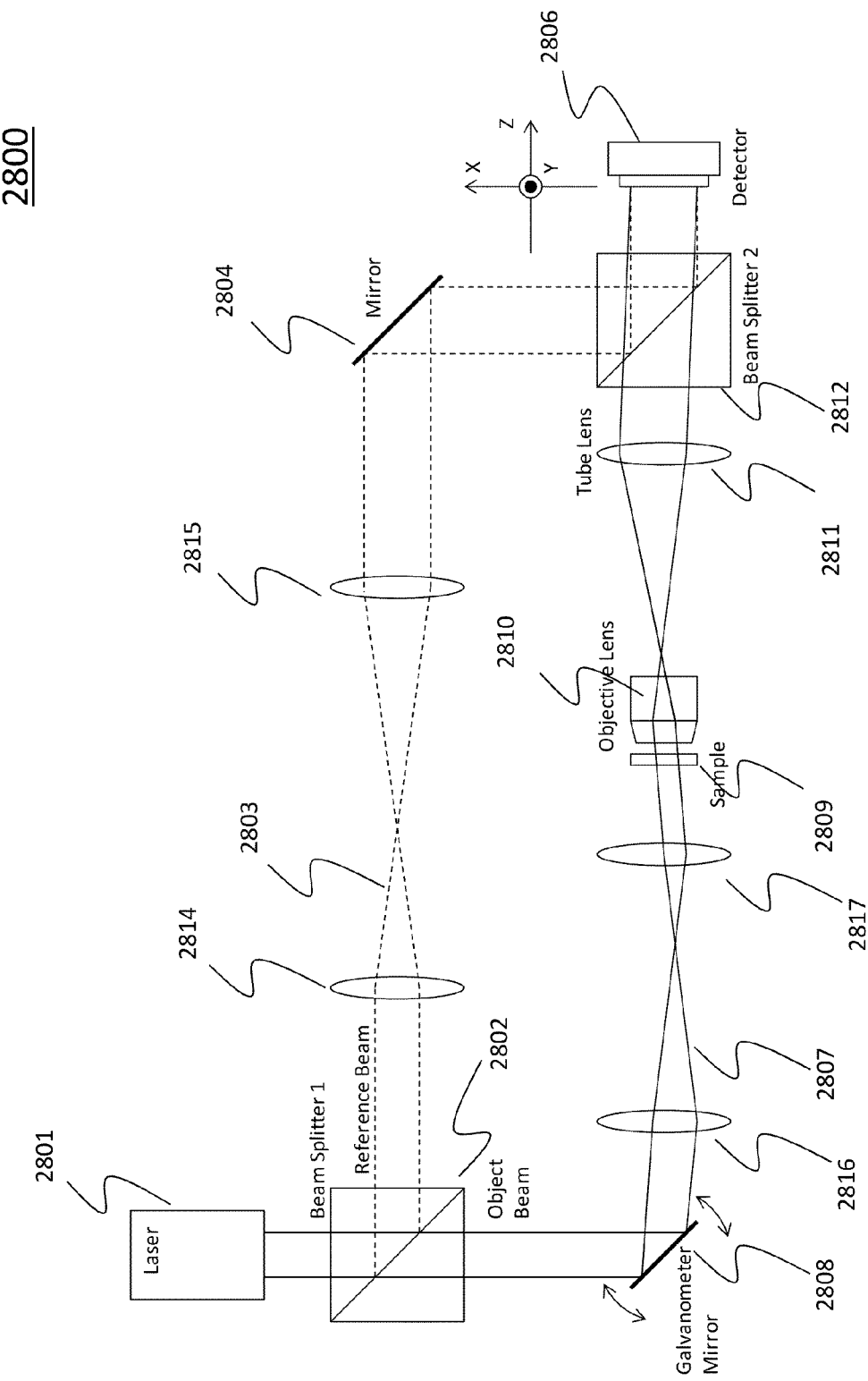
FIG. 20 illustrates a system for the off-axis method.

In FIG. 20, a system 2800 separates an incident light emitted from a laser source 2801 into two beams by a first beam splitter 2802, and integrates them by a second beam splitter 2812. Lens units (2814, 2815, 2816, and 2817) can be used in the system. One beam can be called an object beam 2807, and the other can be called a reference beam 2803. A sample 2809 is located at the object beam side. The object beam 2807 is tilted by a Galvanometer mirror 2808. This tilt makes an angle between the object and reference beams on the detector 2806 in order to generate fringe patterns on the detector 2806. The fringe pattern is recorded as digital holograms.

By changing the angle of the Galvanometer mirror 2808, the incident angle of the object beam 2807 against the sample 2809 can be controlled. By controlling this incident angle, the sample 2809 can be scanned with a lot of angles so that 3D images of the sample 2809 can be reconstructed. The Galvanometer mirror 2808 might move three-dimensionally, or two Galvanometer mirrors might be used for more efficient scanning.

Since this system isn't based on the phase shift method but the off-axis method, a modulator to generate phase shifts, e.g. AOM, is not required. The system 2800 doesn't include this kind of hardware. Accordingly, the system 2800 is simpler than a digital holographic microscope with the phase-shift method.

FIGS. 21A, 21B and 21C show example holograms. The wavelength is 0.543 μm. The shape of the sample is a sphere, whose diameter is 5 μm, and whose refractive index is 1.51. The refractive index in an atmosphere is 1.49. The field size is 13 μm. NA (Numerical Aperture) for the objective lens 2810 is 0.8. FIG. 21A corresponds to a large incident angle δ of the object beam, and FIG. 21C corresponds to a small incident angle of the object beam. FIG. 21B corresponds to a medium incident angle θ of the object beam (between small incident angle δ as shown in FIG. 21C and large incident angle δ as shown in FIG. 21A.

FIGS. 22A, 22B, and 22C show spectrums of the holograms in FIGS. 21A, 21B, and 21C respectively. These spectrums were calculated by numerical Fourier transform.

The light intensity on the detector 2806 is expressed in equation (5).

$$|E_O(x,y)+E_R(x,y)|^2 = |E_O(x,y)|^2 + |E_R(x,y)|^2 + E_O(x,y)E_R^*(x,y) + E_O^*(x,y)E_R(x,y) \quad (5)$$

$E_O(x, y)$ and $E_R(x, y)$ are electric fields for the object and reference beams respectively. The first and second terms correspond to 0th order light (to the center distribution 2201 in FIGS. 22A-C), and the third term corresponds to +1st order light (the right hand side distribution in FIGS. 22A-C), and the fourth term corresponds to −1st order light (the left hand side distribution in FIGS. 22A-C).

The third term can be re-written as follows. We can't see a phase itself because light propagates with a very high speed, but we can see a phase difference. $|\phi(x, y)-\phi_0|$ in the following equation (6) means the phase difference.

$$E_O(x, y)E_R^*(x, y) = |E_O(x, y)|\exp[i\phi(x, y)]\cdot|E_R(x, y)|\exp[-i\phi_0] \quad (6)$$

$$= |E_O(x, y)|\cdot|E_R(x, y)|\exp[i(\phi(x, y)-\phi_0)]$$

The +1st order light can be picked up by using computational apertures 2205, 2206, and 2207 as FIGS. 22A, 22B and 22C, respectively, and Fourier transform of the +1st order light corresponds to the equation above. Thus, phase distribution can be reconstructed.

The finer fringe pattern (larger incident angle) in FIG. 21A makes +1st order light farther away from the 0th order light 2201 in FIG. 22A. The closer +1st order light to 0th order light makes the computational aperture size smaller, because +1st order light can be overlapped in 0th order light. The smaller aperture size means a low resolution because the resolution is proportional to the diameter of the aperture, so smaller incident angle might reduce the resolution.

Figure 23:
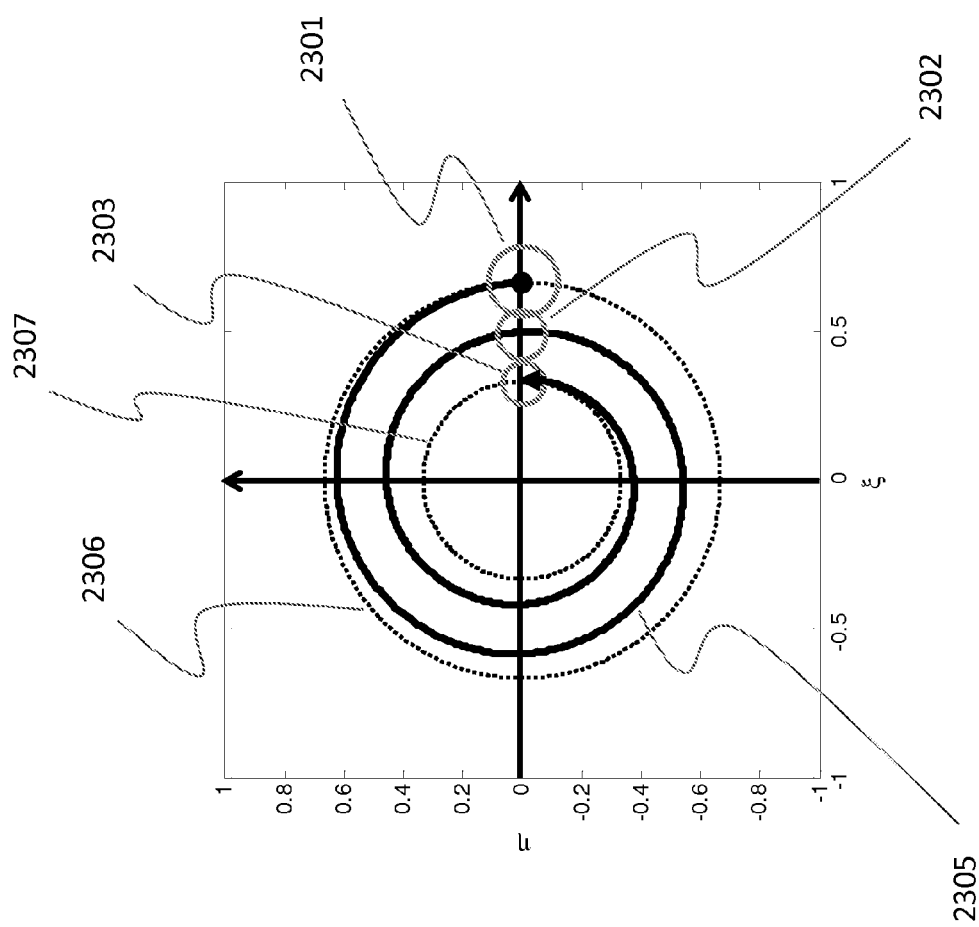
FIG. 23 illustrates a spiral scan.
Figure 24:
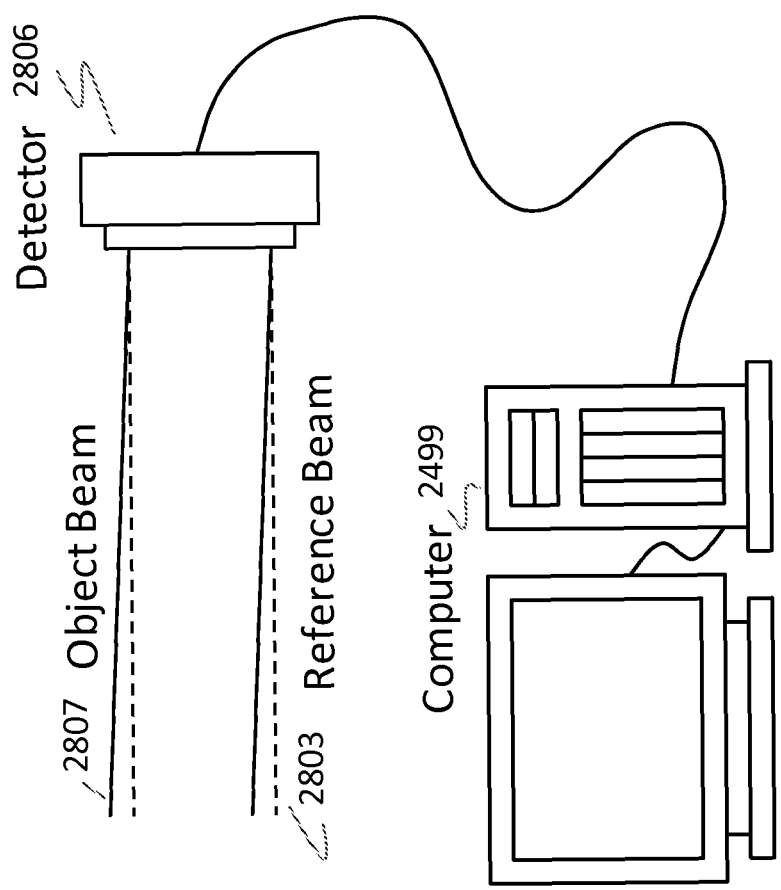
FIG. 24 illustrates a part of digital holographic microscope.

The scanning direction of the object beam is illustrated in FIG. 23. The ξ and η in FIG. 23 correspond to x-axis and y-axis in the Fourier space, respectively. The center position of the computational apertures 2301, 2302, and 2303 to pick up the +1st order light will be moved/rotated while changing the size of the aperture. The arrow 2305 indicates one example to scan the sample with a lot of angles. In short, the angle between the object beam and the optical axis (z) can be gradually decreased while scanning along the direction illustrated by the arrow 2305. Generally the off-axis method uses the fixed computational aperture, but in this present embodiment, the aperture is moved or rotated intentionally by a computational calculation which is executed by a computer as shown in FIG. 24. Thus, the novel system, which uses the incident angle as the off-axis angle efficiently, emerged.

The radius of the aperture center position (dotted lines 2306, 2307 in FIG. 23 might have the maximum and the minimum limitation. The bigger radius means finer fringes in the hologram. The maximum one 2306 might be determined by a pitch of the detector because the detector needs to recognize fringe pattern. The smaller radius makes numerical aperture size smaller. The minimum one 2307 might be determined by the required resolution because the aperture diameter needs to be bigger than one satisfying the required resolution.

To obtain high resolution 3D images, the area inside the smaller dotted circle 2307 should also be scanned. By tilting the reference beam against the detector, fringe patterns on the detector can be acquired in this area.

Figure 25:
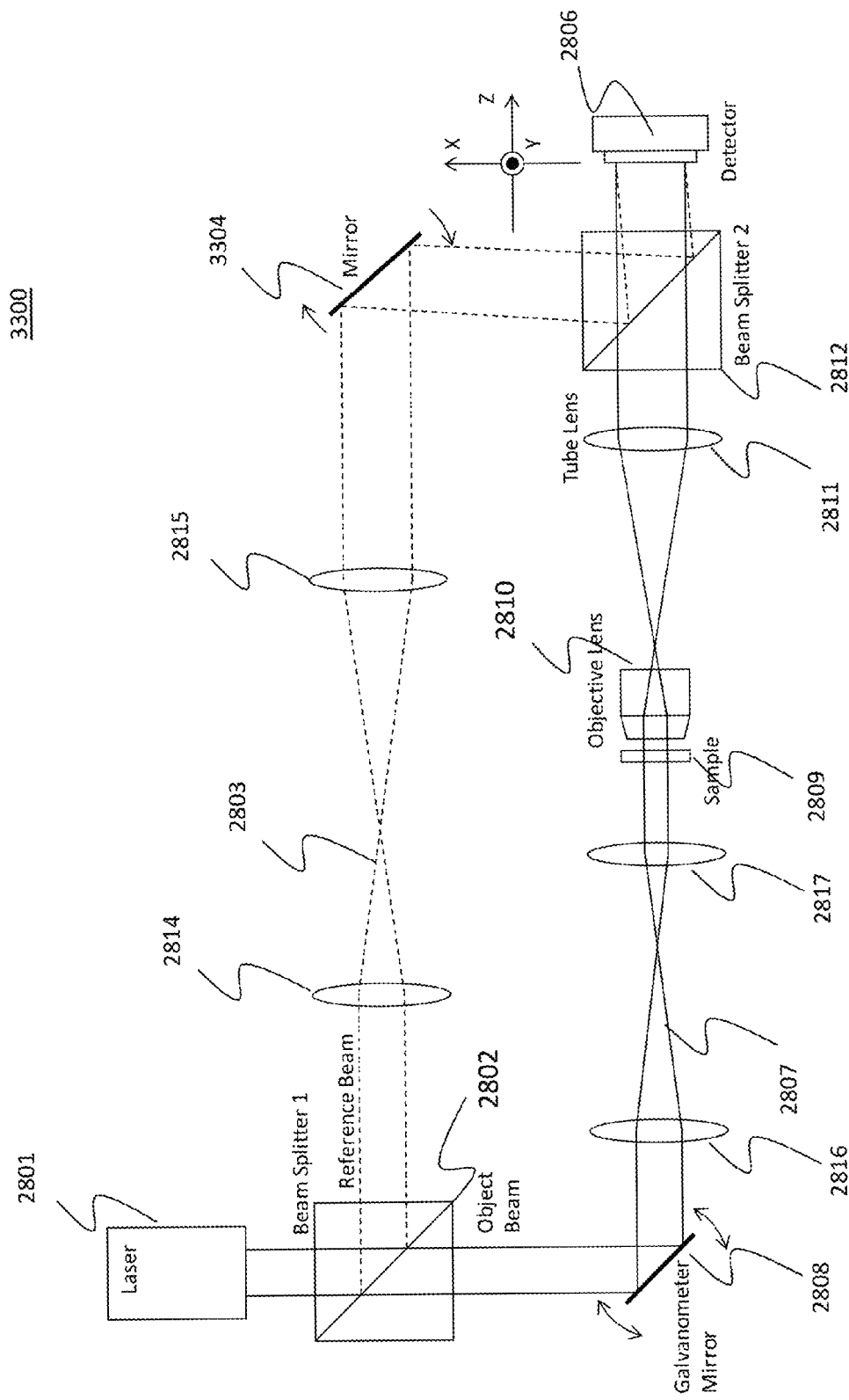
FIG. 25 illustrates a system for an off-axis method.

FIG. 25 shows a system, whose reference beam 2803 is tilted against the detector 2806. This reference beam 2803 can be thought of as the second reference beam. The angle between the normal vector of the detector 2806 and the reference beam 2803 might be very small, e.g. 1~2 degrees, because this angle is not shrunk by the magnification of the objective lens 2810 and the tube lens 2811. When the arrow 2305 in FIG. 23 is on outside of the smaller dotted circle 2307, the configuration in FIG. 20 is used. Then, when the arrow 2305 in FIG. 23 is on inside of the smaller dotted circle 2307, the configuration in FIG. 25 is used in order to shift the origin of the coordinate in FIG. 23. In order to switch quickly between the system in FIG. 20 and the system in FIG. 25, the mirror 3304 might be tilted. The mirror 3304 (2804 in FIG.

20) is used when the arrow is outside of 2307 in FIG. 23, and the mirror 3304 is used when the arrow is inside of 2307 in FIG. 23.

Figure 26:
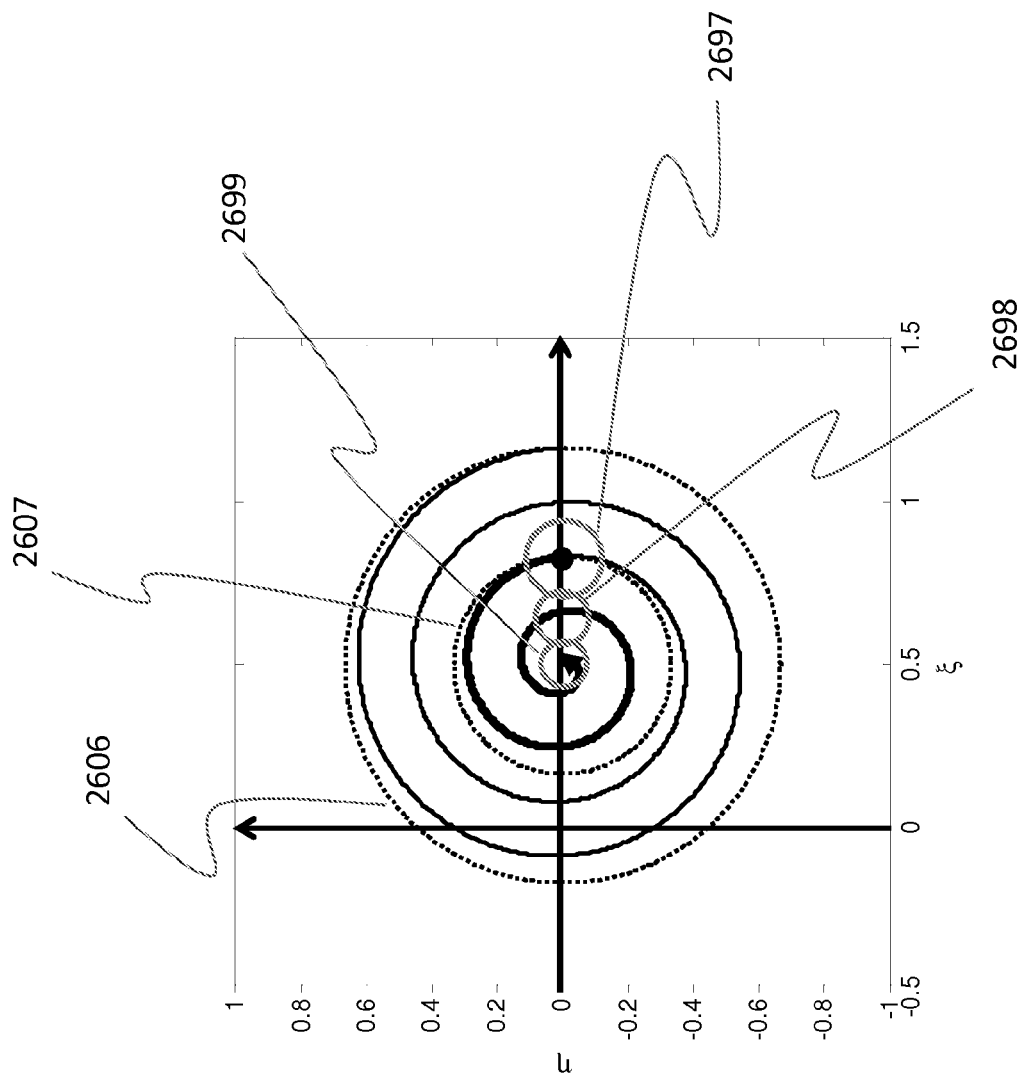
FIG. 26 illustrates centers of computational apertures.

FIG. 26 shows the center positions of the computational apertures (2697, 2698, 2699) to pick up the +1st order light with the configuration shown in FIG. 25. To tilt the reference beam 2803 means to shift the axis η for the spectrum. The diameter of the computational aperture is proportional to the distance between the center of the circle and the origin of the coordinate. Therefore, even if the arrow in FIG. 26 is on inside of the smaller dotted circle 2607, the computational aperture size is big enough to obtain the required resolution.

Third Embodiment

Scanning Both Beams

In this embodiment, a method for controlling an angle of the reference beam while changing an illumination angle of the object beam is described.

Figure 27:
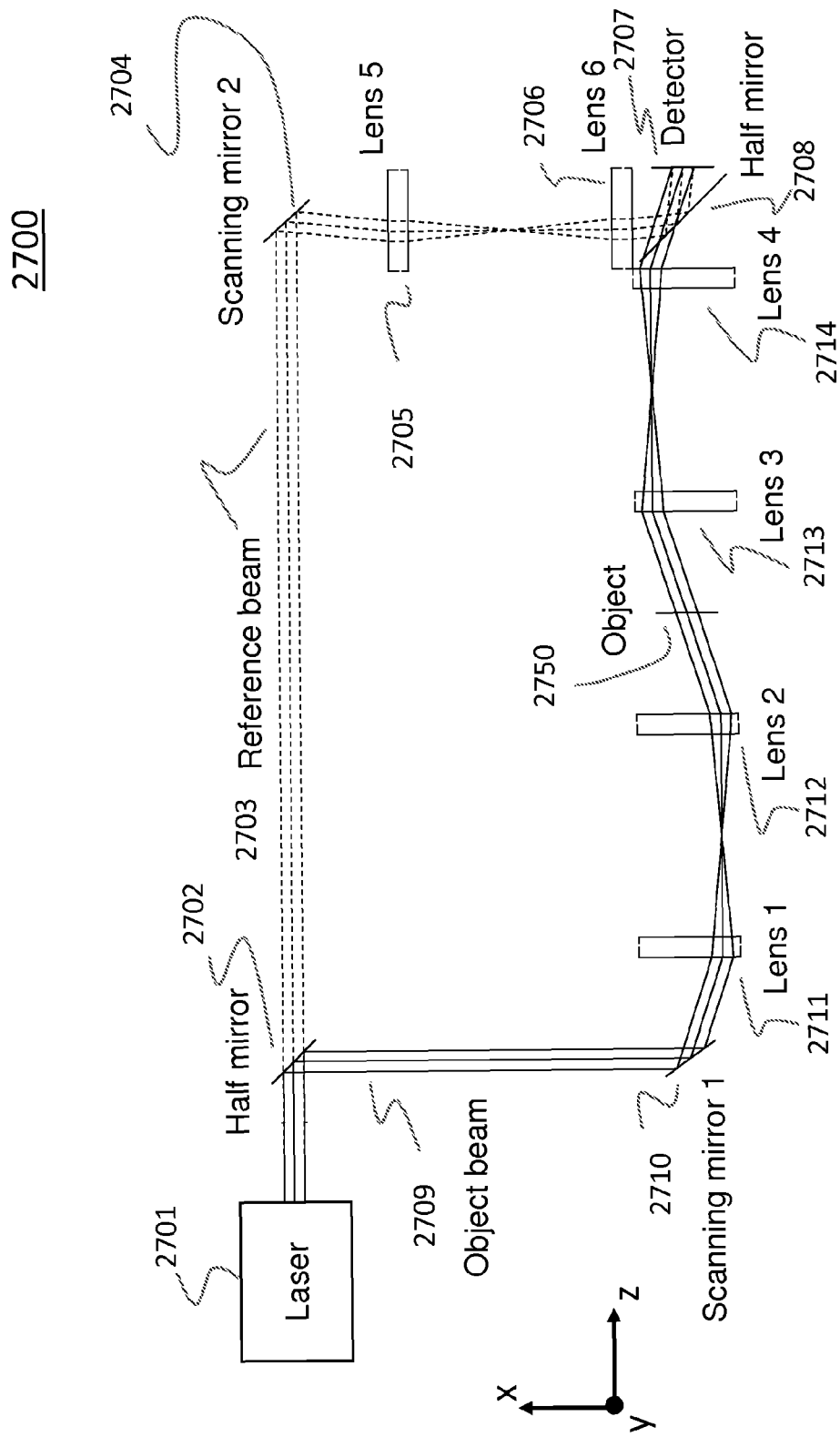
FIG. 27 illustrates an off-axis holography system.

In FIG. 27, the off-axis holography system 2700 is illustrated. A beam from a laser source 2701 is split into an object beam 2709 and a reference beam 2703 by a half mirror 2702. The object beam 2709 travels to a detector 2707 via a scanning mirror 2710, a lens 2711, a lens 2712, an object 2750, a lens 2713, a lens 2714, and a half mirror 2708. The reference beam 2703 travels to the detector 2707 via a scanning mirror 2704, a lens 2705, a lens 2706, and the half mirror 2708. A fringe pattern formed by the object and reference beams can be detected by the detector 2707.

Lenses 1 2711 and 2 2712 make the mirror 2710 and the object 2750 conjugate so that tilting the mirror 2710 doesn't change the position of the beam in the object 2750. A lens 3 2713 is an objective lens, and a lens 4 2714 is a tube lens, and they magnify images. Lenses 5 2705 and 6 2706 change the diameter of the reference beam to match the diameter of the object beam.

A scanning mirror 2710 controls the object beam angle, which is an angle between the object beam and the optical axis, and the scanning mirror 2704 controls the reference beam angle, which is an angle between the reference beam 2703 and the optical axis. In a path of the object beam 2709, a position of a scanning mirror 2710 conjugates with a position of the object 2750, and a position of the object 2750 conjugates with a position of the detector 2707. In a path of the reference beam 2703, a position of the scanning mirror 2704 conjugates with a position of the detector 2707.

A relative angle between the object beam 2709 and the reference beam 2703 is not constant and rather the angle varies in order to keep the fringe pitch d constant while scanning.

Figure 28:
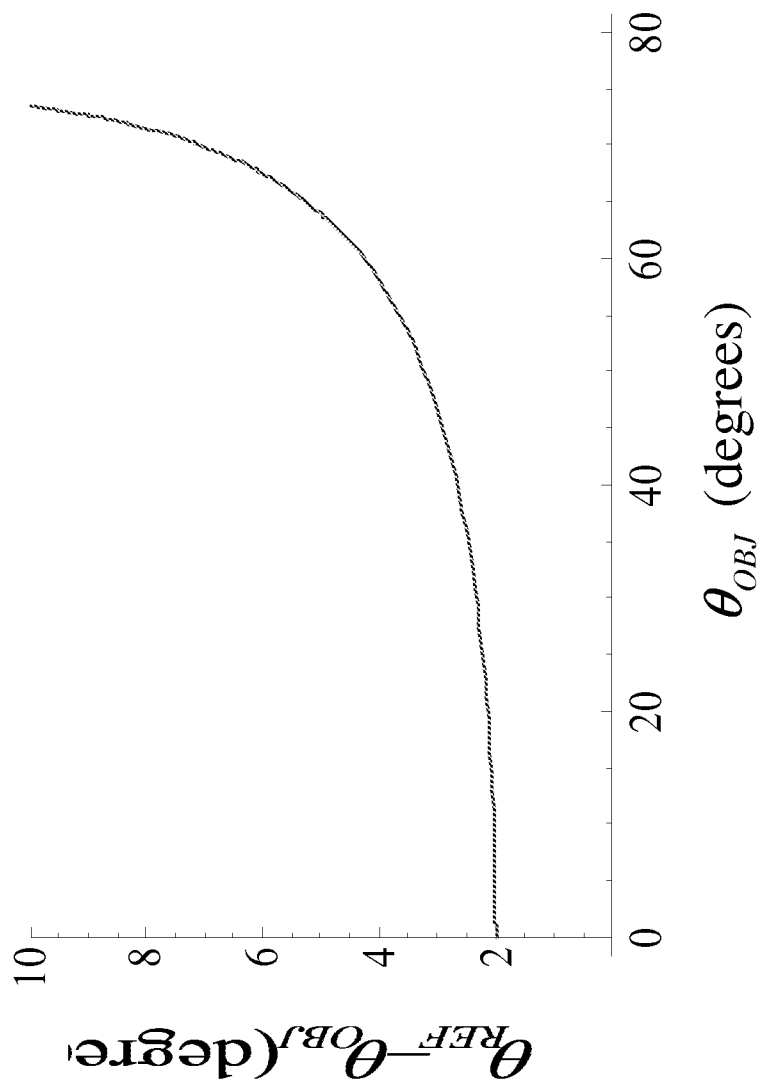
FIG. 28 illustrates a relationship between the incident angle of the object beam ($\theta_{OBJ}$) and the incident angle of the reference beam ($\theta_{REF}$).

FIG. 28 shows the relationship between $\theta_{OBJ}$ and $\theta_{REF}$ to keep the fringe pitch constant. λ=543 nm and d=15.6 μm are assumed for the calculation. In this embodiment, the angle of the object beam 2709 is changed with a constant interval, and the angle of the reference beam 2703 is controlled independently to satisfy the following equation (7):

$$d = \frac{\lambda}{|\sin \theta_{REF} - \sin \theta_{OBJ}|} \quad (7)$$

Even if the angle of the object beam 2709 is changed while scanning, the pitch of the fringe is maintained unless the relation between $\theta_{OBJ}$ and $\theta_{REF}$ varies based on the relation as illustrated in FIG. 28. In the system in the second embodiment, each fringe pitch will be changed due to the spiral scanning, but if the reference beam is also scanning according to the spiral scanning of the object beam, the each fringe pitch will be kept constant.

Figure 29:
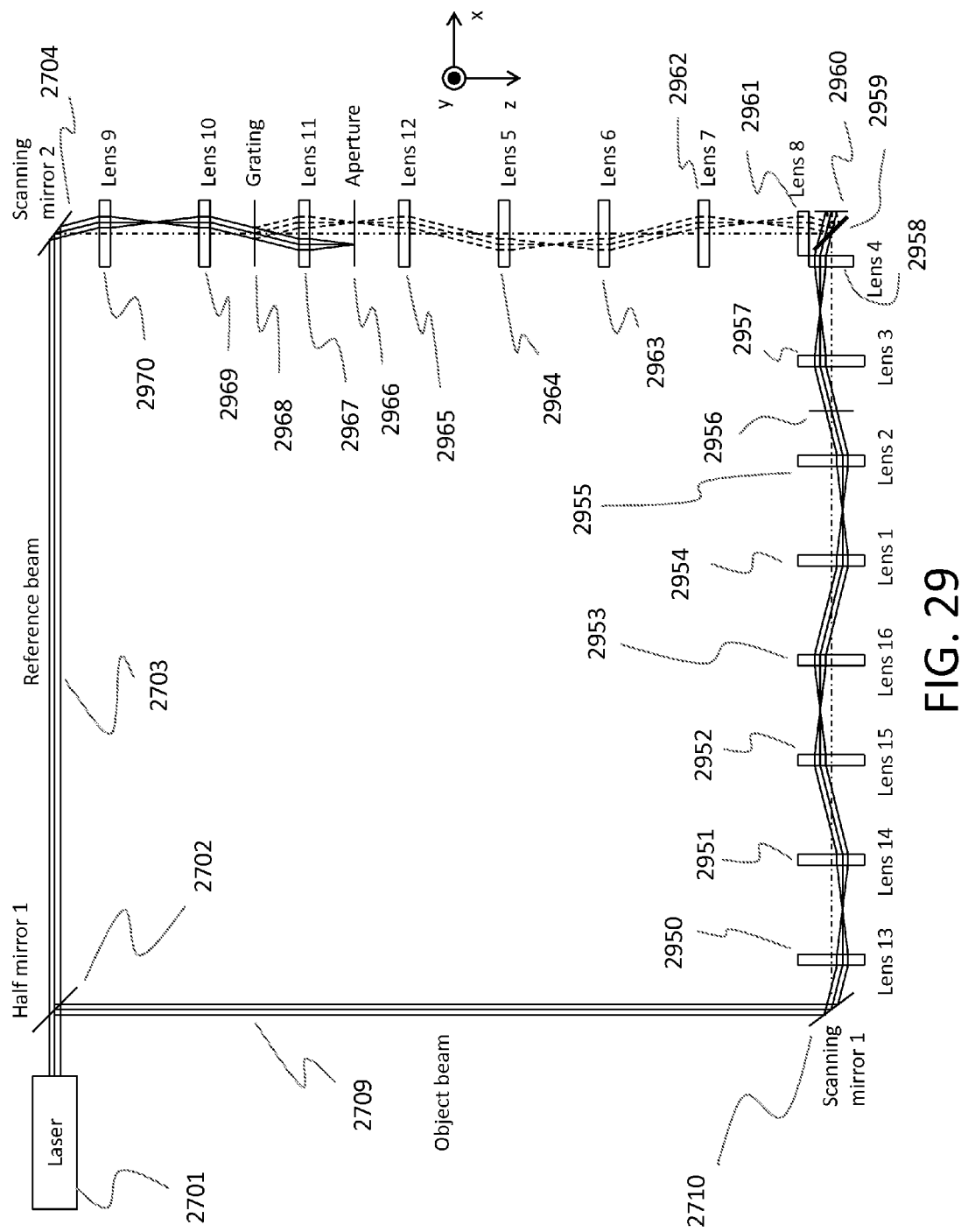
FIG. 29 illustrates an off-axis holography system.

In FIG. 29, another off-axis holography system is illustrated. A light beam from a laser 2701 is split into an object beam 2709 and a reference beam 2703. The object beam 2709 travels to a detector 2960 via a scanning mirror 2710, a lens group (2950, 2951, 2952, 2953, 2954, and 2955), an object 2956, a lens 2957, a lens 2958, and a half mirror 2959. The reference beam 2703 travels to the detector 2960 via a scanning mirror 2704, a lens 2970, a lens 2969, a grating 2968, a lens 2967, an aperture 2966, a lens group (2965, 2964, 2963, 2962, and 2961), and the half mirror 2959.

The scanning mirror can be moved while maintaining the relation between $\theta_{OBJ}$ and $\theta_{REF}$ which as described in the above embodiment.

The angles of the scanning mirrors 2710 and 2704 can be synchronized in this embodiment. The 1st order diffraction beam created by the grating 2968 and spatially filtered by the aperture 2966 is used as the reference beam 2703. The aperture 2966 blocks all the other order diffraction beams.

The position of diffraction beams in the aperture 2966 will be shifted by scanning of the mirror 2704. When the grating has slits along y-axis and the scanning direction is parallel to x-axis, an area for the 1st order diffraction beam may be overlapped with an area for the other order diffraction beams during scanning. The area for the 1st order diffraction should be separated in order to block all the other order diffraction beams.

Figures 30A, 30B:
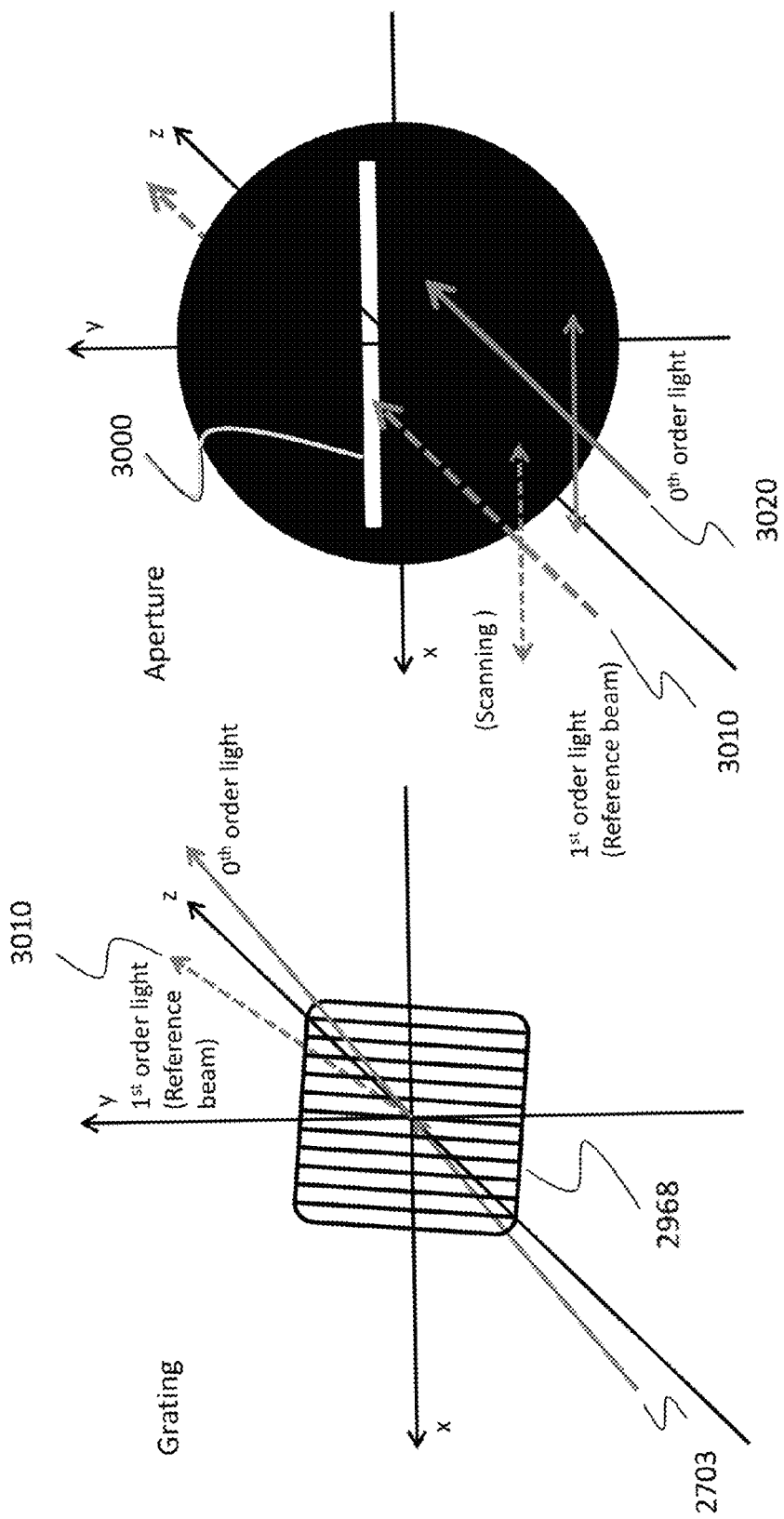
FIG. 30A illustrates a grating.
FIG. 30B illustrates an aperture.

FIG. 30A shows a slightly tilted grating 2968 against y-axis. By this slight tilt, the area for each order diffraction beam in the aperture position is shifted along y-axis. FIG. 30B shows one example of the aperture 3000 to block all order diffraction beams (ex. $0_{th}$ order light 3020) except for the 1st order diffraction beam 3010. If a distortion caused by the grating is remarkable, the aperture shape may be modified. The blank position in larger |x| may be at slightly larger |y|.

In the reference beam path, a position of the grating 2968 conjugates with a position of the scanning mirror 2704, and a position of the scanning mirror 2704 conjugates with a position of the detector 2960.

In the object beam path, a position the scanning mirror 2710 conjugates with a position of the object 2956, and a position of the object 2956 conjugates with a position of the detector 2960.

The angles of the scanning mirrors 2710 and 2704 can be changed simultaneously with same increment while scanning. Then, the fringe pitch created on the detector is kept constant. The fringe pitch created on the detector 2960 is determined by a pitch of the grating 2968. In other words by using a relation in the following equation (8), the equation for the pitch of the fringe pattern can be written as equation (9).

$$\sin \theta_{REF} - \sin \theta_{OBJ} = \frac{\lambda}{L} \quad (8)$$

where L is the grating pitch. Then, Eq. (7) can be re-written as $$d = \frac{\lambda}{|\sin \theta_{REF} - \sin \theta_{OBJ}|} = \frac{\lambda}{\lambda/L} = L \quad (9)$$

Therefore, the fringe pitch created on the detector 2960 is determined by the grating pitch of the grating 2968.

Figure 31:
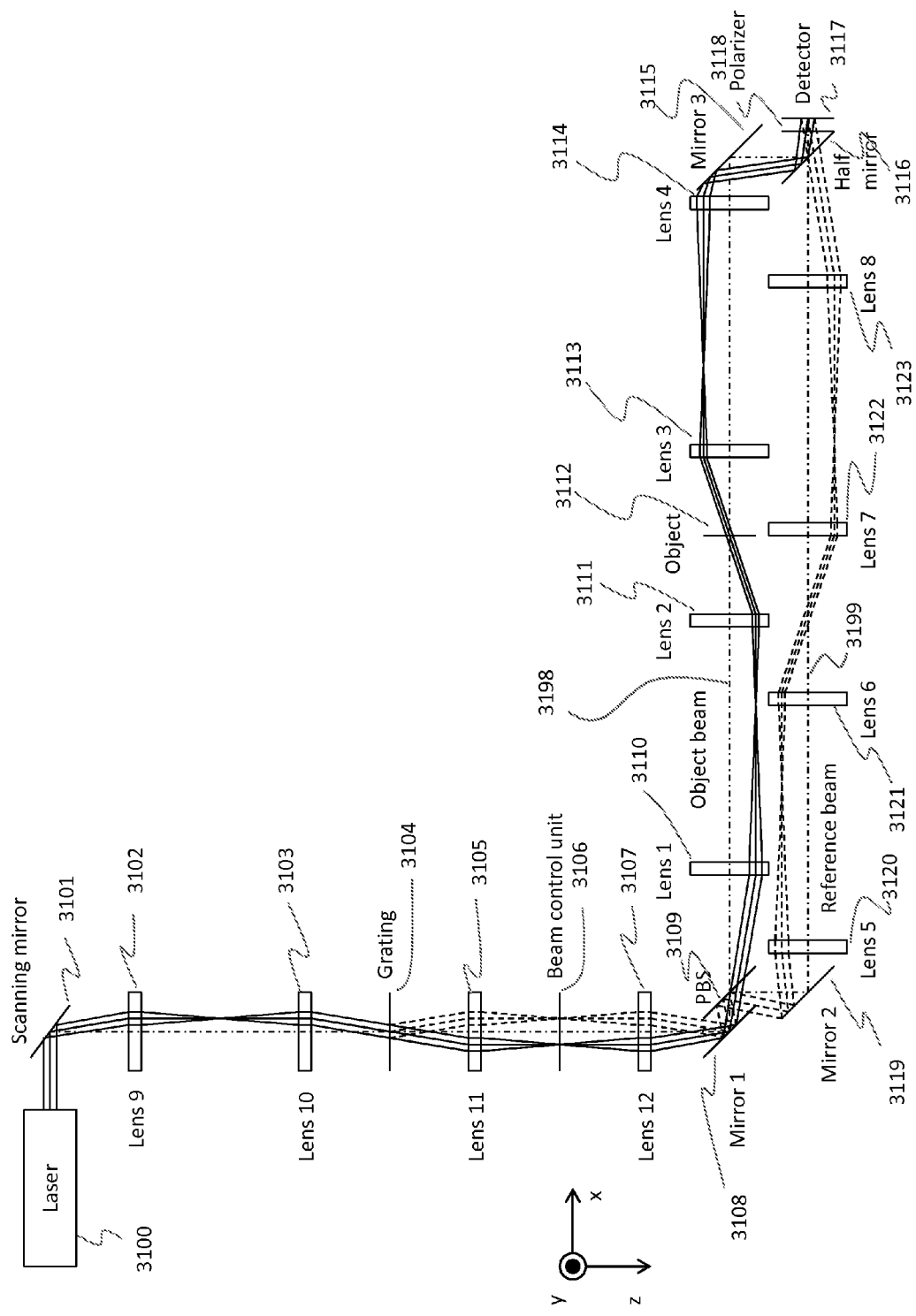
FIG. 31 illustrates another system for an off-axis method.

In another embodiment illustrated in FIG. 31, only one scanning mirror is necessary to change both the angles for the object and the reference beams.

A beam from a laser 3100 can be scanned by a scanning mirror 3101 and is input into a grating 3104 via a lens 3102 and a lens 3103. $0^{th}$ and $1^{st}$ order diffraction beams travel to a beam control unit 3106 via a lens 3105.

The $0_{th}$ order diffraction beam is used as the object beam 3198 and the $1_{st}$ order diffraction beam is used as the reference beam 3199. These beams travel to the detector via a mirror 3108, and a PBS (polarization beam splitter) 3109. The beam control unit 3106 has three functions: (i) Blocking the diffraction beams other than the $0_{th}$ and $1_{st}$ orders, (ii) Changing the polarization state of the object beam ($0_{th}$ order beam) 3198 to p-polarization (polarization vector is in the plane of the figure), and (iii) Changing the polarization state of the reference beam ($1_{st}$ order beam) 3199 to s-polarization (polarization vector is perpendicular to the plane of the figure).

The two beams are separated by the PBS 3109 that transmits the p-polarization and reflects the s-polarization. A linear polarizer 3118 is inserted before the detector 3117 to maximize the contrast of a fringe pattern created by the interference of the two beams. The object beam 3198 (p-polarization) travels to the detector 3117 via a lens 3110, a lens 3111, an object 3112, a lens 3113, a lens 3114, a mirror 3115, a half mirror 3116, and the polarizer 3118. The reference beam 3199 (s-polarization) travels to the detector 3117 via the PBS 3109, a mirror 3119, a lens 3120, a lens 3121, a lens 3122, a lens 3123, the half mirror 3116, and the polarizer 3118.

The potions between the grating 3104 and the scanning mirror 3101 are conjugate, so that the incident beam into the grating 3104 isn't shifted along x direction even if the scanning mirror 3101 is tilted.

A position of the grating 3104 conjugates with the detector 3117 so that the fringe pitch created on the detector 3117 is determined by the grating pitch, and the fringe pitch created on the detector is kept constant.

Figures 32A, 32B:
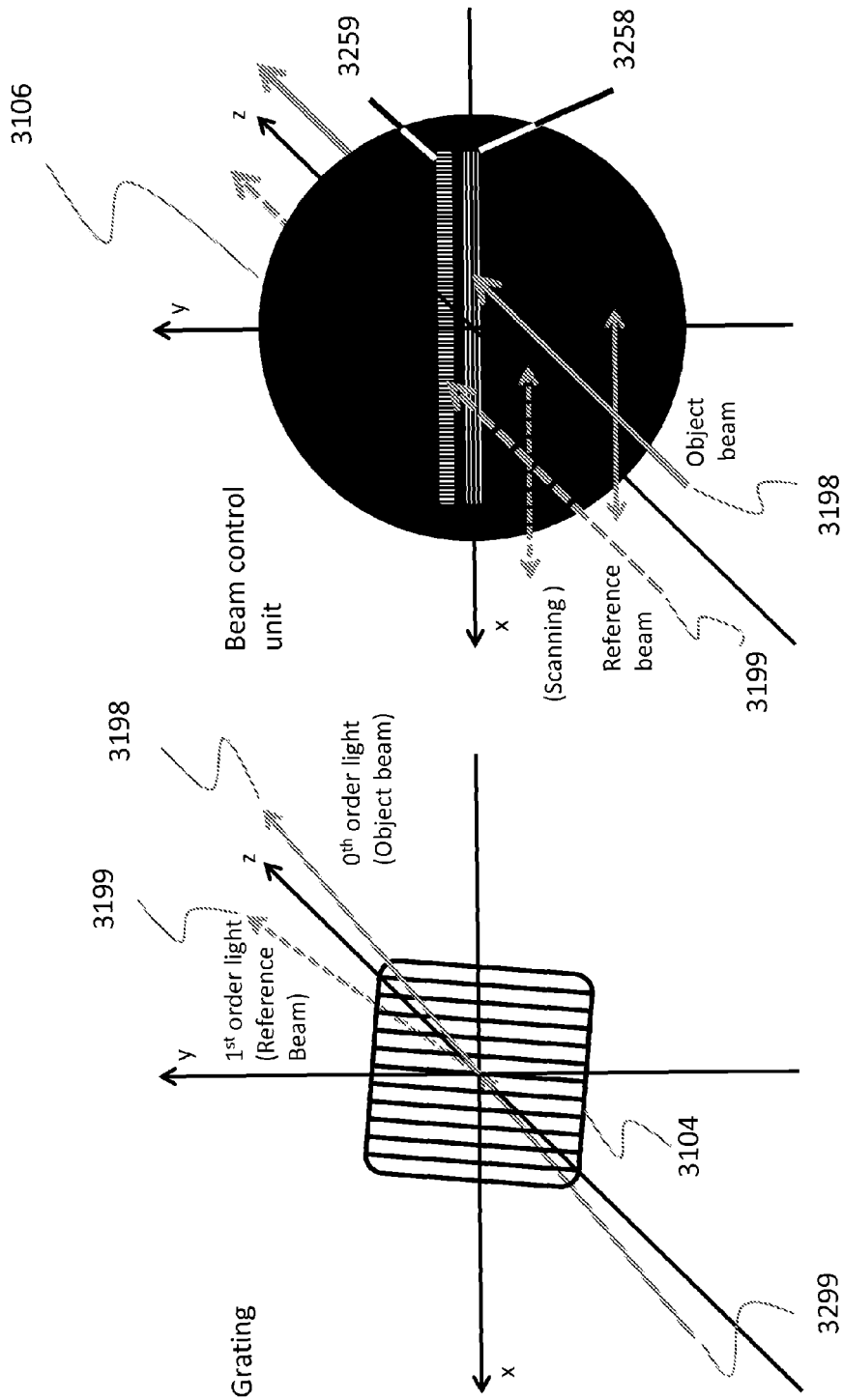
FIG. 32A illustrates a grating.
FIG. 32B illustrates a beam control unit

FIG. 32A shows one example of the grating 3104. The purpose of tilting is the same as the previous embodiment illustrated in FIG. 30A. The grating 3104 forms at least $0^{th}$ order diffraction beam for the object beam 3198 and $1^{st}$ order diffraction beam for the reference beam 3199 according to the incident beam 3299.

FIG. 32B shows one example of the beam control unit 3106. A polarizer 3258 to change the polarization state of the object beam 3198 to p-polarization is located at y=0, and a polarizer 3259 to change the polarization state of the reference beam 3199 to s-polarization is located at slightly higher position from y=0.

While the embodiments according to the present invention have been described with reference to exemplary embodiments, it is to be understood that the present invention is not limited to the above described embodiments. The scope of the following claims is to be accorded the broadest interpretation so as to encompass all such modifications and equivalent structures and functions.

What is claimed is:

1. An interferometric method for detecting information about a sample comprising;
    emitting a laser beam;
    splitting the laser beam into a reference beam and an object beam;
    transmitting the object beam through the sample at an incident angle;
    combining the reference beam with the object beam passed through the sample to form an interference pattern;
    detecting the interference pattern, and
    non-linearly scanning the object beam in order to detect a plurality of interference patterns and to reconstruct a three-dimensional image of the sample.

2. The interferometric method according to claim 1, further comprising storing data of the detected interference patterns for use in reconstructing the three-dimensional image of the sample by using the stored data.

3. The interferometric method according to claim 2, further comprising:
    calculating a spatial frequency spectrum based on the stored data; and
    obtaining specified information from the spatial frequency spectrum by using a computational aperture to reconstruct the three-dimensional image of the sample.

4. The interferometric method according to claim 3, wherein the computational aperture is moved according to the non-linear scanning.

5. The interferometric method according to claim 3, wherein:
    the non-linear scanning is spiral scanning; and
    a size of the computational aperture is changed according to a change of the incident angle during the scanning.

6. The interferometric method according to claim 3, wherein the non-linear scanning is spiral scanning.

7. The interferometric method according to claim 1, wherein the non-linear scanning is circular scanning.

8. The interferometric method according to claim 7, wherein the incident angle of the object beam is maintained while scanning so that each interference pattern has the substantially same fringe pitch.

* * * * *

UNITED STATES PATENT AND TRADEMARK OFFICE
CERTIFICATE OF CORRECTION

PATENT NO. : 8,896,840 B2
APPLICATION NO. : 13/455931
DATED : November 25, 2014
INVENTOR(S) : Isao Matsubara et al.

It is certified that error appears in the above-identified patent and that said Letters Patent is hereby corrected as shown below:

Title page, item [73],
Assignees should be:
Canon Kabushiki Kaisha; and
The Arizona Board of Regents on Behalf of the University of Arizona Signed and Sealed this
Eighteenth Day of August, 2015

Michelle K. Lee
*Director of the United States Patent and Trademark Office*